(12) United States Patent
Ma et al.

(10) Patent No.: US 10,960,095 B2
(45) Date of Patent: *Mar. 30, 2021

(54) SYSTEMS AND METHODS TO MONITOR PROPER DISINFECTION OF NEEDLELESS CONNECTORS

(71) Applicant: Becton, Dickinson and Company, Franklin Lakes, NJ (US)

(72) Inventors: Yiping Ma, Layton, UT (US); S. Ray Isaacson, Layton, UT (US)

(73) Assignee: Becton, Dickinson and Company, Franklin Lakes, NJ (US)

( * ) Notice: Subject to any disclaimer, the term of this patent is extended or adjusted under 35 U.S.C. 154(b) by 0 days.

This patent is subject to a terminal disclaimer.

(21) Appl. No.: 16/356,957

(22) Filed: Mar. 18, 2019

(65) Prior Publication Data

US 2019/0209726 A1  Jul. 11, 2019

Related U.S. Application Data

(63) Continuation of application No. 14/078,027, filed on Nov. 12, 2013, now Pat. No. 10,251,965, which is a
(Continued)

(51) Int. Cl.
*A61M 39/16* (2006.01)
*A61L 2/18* (2006.01)
(Continued)

(52) U.S. Cl.
CPC ............... *A61L 2/24* (2013.01); *A61L 2/16* (2013.01); *A61L 2/18* (2013.01); *A61M 39/16* (2013.01); *A61M 39/162* (2013.01); *B08B 1/006* (2013.01); *B08B 1/04* (2013.01); *B08B 3/08* (2013.01); *G06K 7/10009* (2013.01); *G16H 10/60* (2018.01); *G16H 40/63* (2018.01);
(Continued)

(58) Field of Classification Search
CPC ............ A61L 2202/14; A61L 2202/17; A61L 2202/24; A61L 2/16; A61L 2/18; A61L 2/24; A61M 39/16; A61M 39/162; B08B 1/006; B08B 1/04; B08B 3/08; G06K 7/10009; G16H 10/60; G16H 40/63
See application file for complete search history.

(56) References Cited

U.S. PATENT DOCUMENTS

| 3,390,412 A | 7/1968 | Wolter et al. |
| 5,251,356 A | 10/1993 | Oaki et al. |

(Continued)

FOREIGN PATENT DOCUMENTS

WO  2011/061544  5/2011

*Primary Examiner* — Douglas Lee
(74) *Attorney, Agent, or Firm* — Kirton & McConkie; Craig Metcalf; Kevin Stinger

(57) ABSTRACT

A device and method for disinfecting a needleless connector, the device including a housing comprising a hub rotationally coupled to a motor, the motor being operably connected to a power source, the hub further comprising a receptacle configured to receive a cleaning head, wherein the device is configured to detect achievement of one or more minimum thresholds which are recommended to achieve proper disinfection of the needleless connector. Various devices and methods are further provided to permit tracking and reporting of disinfection events.

18 Claims, 19 Drawing Sheets

Related U.S. Application Data continuation of application No. 13/904,285, filed on May 29, 2013, now Pat. No. 9,216,440.

(60) Provisional application No. 61/653,938, filed on May 31, 2012, provisional application No. 61/653,943, filed on May 31, 2012, provisional application No. 61/653,949, filed on May 31, 2012.

(51) Int. Cl.
*B08B 1/04* (2006.01)
*A61L 2/16* (2006.01)
*B08B 1/00* (2006.01)
*B08B 3/08* (2006.01)
*A61L 2/24* (2006.01)
*G06K 7/10* (2006.01)
*G16H 40/63* (2018.01)
*G16H 10/60* (2018.01)

(52) U.S. Cl.
CPC ....... *A61L 2202/14* (2013.01); *A61L 2202/17* (2013.01); *A61L 2202/24* (2013.01)

(56) References Cited

U.S. PATENT DOCUMENTS

| | | |
|---|---|---|
| 5,493,747 A | 2/1996 | Inakagata et al. |
| 6,493,896 B1 | 12/2002 | Stuchlik et al. |
| 6,961,974 B1 | 11/2005 | Goolsby, Jr. |
| 7,603,739 B2 | 10/2009 | Minkler et al. |
| 9,216,440 B2 | 12/2015 | Ma et al. |
| 9,782,507 B2 | 10/2017 | Ma et al. |
| 10,251,965 B2 * | 4/2019 | Ma .................. A61M 39/16 |
| 2003/0046780 A1 | 3/2003 | Davis |
| 2004/0187889 A1 | 9/2004 | Kemp et al. |
| 2004/0255414 A1 | 12/2004 | Tulipana |
| 2004/0260201 A1 | 12/2004 | Mueller |
| 2005/0177964 A1 | 8/2005 | Cisneros |
| 2005/0197646 A1 | 9/2005 | Connel et al. |
| 2006/0076035 A1 | 4/2006 | McGee et al. |
| 2008/0019889 A1 | 1/2008 | Rogers et al. |
| 2008/0031678 A1 | 2/2008 | Gansebom et al. |
| 2008/0034515 A1 | 2/2008 | Hilscher et al. |
| 2008/0038167 A1 | 2/2008 | Lynn |
| 2008/0147047 A1 | 6/2008 | Davis et al. |
| 2009/0028750 A1 | 1/2009 | Ryan |
| 2010/0043156 A1 | 2/2010 | Kressner |
| 2010/0095973 A1 | 4/2010 | Shrier |
| 2010/0101032 A1 | 4/2010 | Kressner |
| 2010/0145721 A1 | 6/2010 | Deshays |
| 2010/0200017 A1 | 8/2010 | Kerr et al. |
| 2011/0030726 A1 | 2/2011 | Vaillancourt et al. |
| 2011/0106019 A1 | 5/2011 | Bagwell et al. |
| 2011/0197921 A1 | 8/2011 | Rubin et al. |
| 2011/0224649 A1 | 9/2011 | Duane et al. |
| 2011/0284024 A1 | 11/2011 | Trebella et al. |

\* cited by examiner

SYSTEMS AND METHODS TO MONITOR PROPER DISINFECTION OF NEEDLELESS CONNECTORS

RELATED APPLICATIONS

This application is a continuation of U.S. application Ser. No. 14/078,027, filed Nov. 12, 2013, titled SYSTEMS AND METHODS TO MONITOR PROPER DISINFECTION OF NEEDLELESS CONNECTORS, which is a continuation of U.S. application Ser. No. 13/904,285, filed May 29, 2013, titled SYSTEMS AND METHODS TO MONITOR PROPER DISINFECTION OF NEEDLELESS CONNECTORS, which claims priority to U.S. Provisional Patent Application Ser. Nos. 61/653,926, filed May 31, 2012, titled SYSTEMS AND METHODS FOR DISINFECTING NEEDLELESS CONNECTORS; 61/653,938, filed May 31, 2012, titled DISPOSABLE DISINFECTION CLEANING HEAD; 61/653,943, filed May 31, 2012, titled SYSTEMS AND METHODS TO CONTROL PROPER DISINFECTION OF NEEDLELESS CONNECTORS; and 61/653,949, filed May 31, 2012, titled SYSTEMS AND METHODS TO MONITOR PROPER DISINFECTION OF NEEDLELESS CONNECTORS, which are incorporated herein in their entirety.

BACKGROUND OF THE INVENTION

The present invention relates to systems and methods for disinfecting a needleless connector. In particular, the present invention relates to a disinfection device comprising monitoring and feedback circuitry which monitors various minimum thresholds to ensure proper contact between a needleless connector and a cleaning head of the disinfection device. In some instances, a disinfection device further comprises a status indicator which communicates a status or level of disinfection of the needleless connector to a user.

One of the major challenges of modern medical treatment is control of infection and the spread of microbial organisms. One area where this challenge is constantly presented is in infusion therapy of various types. Infusion therapy is one of the most common health care procedures. Hospitalized, home care, and other patients receive fluids, pharmaceuticals, and blood products via a vascular access device inserted into the vascular system. Infusion therapy may be used to treat an infection, provide anesthesia or analgesia, provide nutritional support, treat cancerous growths, and maintain blood pressure and heart rhythm, or many other clinically significant uses.

Infusion therapy is facilitated by an intravenous (IV) administration set. The IV administration set may access a patient's peripheral or central vasculature. The IV administration set may be indwelling for short term (days), moderate term (weeks), or long term (months to years). The IV administration set may be used for continuous infusion therapy or for intermittent therapy.

A common component of an IV administration set is a plastic catheter that is inserted into a patient's vein. The IV administration set may further include various connectors and fittings with further facilitate intravenous access and communication. For example, an IV administration set may include a needleless Luer adapter to which other medical devices may be attached. Commonly, an IV administration set comprises one or more vascular access devices that may be attached to another vascular access device, closes the vascular access device, and allows for intermittent infusion or injection of fluids and pharmaceuticals. An IV administration set may further include a housing and a septum for closing the system. The septum may be opened with a needleless connector, such as a blunt cannula or a male Luer of a medical device.

An IV administration set may serve as a nidus of infection, resulting in a disseminated BSI (blood stream infection). In some instances, this may be caused by insufficient disinfection of the various connectors and other access components of the IV administration set. Generally, disinfection of needleless connectors and other access components of the IV administration set is accomplished through manual scrubbing using a disinfection swab or pad. However this process varies greatly from clinician to clinician both in terms of duration and contact forces. These variations lead to inconsistent disinfection which may encourage bacterial growth and infection. Further, the methods are untraceable and therefore lack the ability to monitor which needleless connectors have been disinfected.

Thus, while techniques currently exist that are used for disinfecting needleless connectors and other access components of an IV administration set, challenges still exist. Accordingly, it would be an improvement in the art to augment or even replace current techniques with other techniques.

BRIEF SUMMARY OF THE INVENTION

The present invention relates to systems and methods for disinfecting a needleless connector, PRN, or other access components of an IV administration set. In particular, the present invention relates to a disinfection device comprising monitoring and feedback circuitry which monitors various minimum thresholds to ensure proper contact time and pressure between a needleless connector and a cleaning head of the disinfection device. In some instances, a disinfection device further comprises a status indicator which communicates a status or level of disinfection of the needleless connector to a user.

Some implementations of the present invention provide a device for disinfecting a needleless connector of an IV administration set, wherein the disinfection device includes a housing in which is housed a hub rotationally coupled to a motor. The motor is further operably connected to a power source, such as an internal battery. In some instances, the hub further includes a receptacle or socket configured to receive a cleaning head. In some implementations, the cleaning head comprises a disposable unit. The disinfection device further includes a pressure-sensitive switch which is positioned and configured to detect a pressure between the cleaning head and a needleless connector, the pressure-sensitive switch comprising a minimum pressure threshold that must be met or exceeded to activate the motor.

A disinfection device of the present invention may further include a status indicator which is configured to display a disinfection status of the needleless connector. In some instances, the status indicator includes one or more lights which display a color or lighted pattern to indicate the status of disinfection.

Various aspects of the present invention include one or more minimum thresholds which must be met or accomplished to achieve complete or satisfactory disinfection of the needleless connector. In some instances, the motor comprises a minimum rotational threshold. In other instances, the axial load-sensitive switch comprises a minimum axial load threshold, wherein the minimum axial load threshold is a minimum axial load between the cleaning head of the disinfection device and the needleless connector to achieve complete disinfection. In some instances, the axial load can be the axial force or pressure.

Some implementations of the present invention further include a motor that is capable of oscillatory rotational motions at certain frequencies such that the cleaning head with disinfect the needleless connector in a back and forth motion.

Some implementations of the present invention further include a timer which is configured to measure a lapse or length of time over which the minimum threshold is maintained. In some instances, the timer is operably connected to the status indicator, such that upon detecting completion of a minimum time lapse threshold, the timer signals to the status indicator that is sufficient disinfection has been achieved. In turn, the status indicator provides a signal to indicate complete disinfection.

Some aspects of the present invention further include a method for controlling proper disinfection of a needleless connector the method including steps for 1) providing a disinfecting device comprising a minimum threshold to indicate a proper interaction between the disinfecting device and a needleless connector; 2) detecting the minimum threshold; 3) detecting a minimum disinfection time threshold of the disinfecting device; and 4) indicating a status of disinfection. For some methods, the minimum threshold comprises a minimum rotational torque of a motor of the disinfecting device. For other methods, the minimum threshold comprises a minimum pressure threshold of a pressure-sensitive switch of the disinfecting device. Further, for some methods the minimum pressure threshold indicates proper pressure between the cleaning head and the needleless connector. In some instances, the minimum rotational torque is determined by a minimum current of the motor.

Some aspects of the present invention further include a method for determining proper disinfection of a needleless connector, the method including steps for 1) sensing a minimum contact threshold between the needleless connector and a cleaning head of a disinfecting device; 2) sensing a length of time for which the minimum contact threshold is maintained; and 3) indicating a status of disinfection based upon the length of time for which the minimum contact threshold is maintained.

Some implementations of the present invention further include a device for disinfecting a needleless connector, the device comprising a housing having a hub rotationally coupled to a motor, the motor being operably connected to a power source the hub further including a receptacle configured to receive a cleaning head, the device further including a pressure-sensitive switch configured to detect a pressure between the cleaning head and the needleless connector, the pressure-sensitive switch comprising a minimum pressure threshold that must be met or exceeded to activate the motor. The device further includes an input for receiving an identification of the needleless connector and/or the cleaning head, and an output for communicating the identification and a disinfection status of the needleless connector and/or the cleaning head. The tracking of the cleaning head can be important in case where the cleaning head is to be used only once. In some instances, the output comprises at least one of a wireless antenna, an electrical connector, an RFID transmitter, and a Bluetooth transmitter. In other instances, the input comprises at least one of a barcode scanner, an optical camera, and a magnetic card reader. The disinfection device further comprises a network operably connected to the output whereby information retrieved by the disinfection device is transferred to a remote computer device and subsequently stored in electronic medical record of the patient for whom the needleless connector was disinfected.

Some aspects of the present invention further include a method for monitoring and recording disinfection information of a needleless connector, the method including steps for 1) receiving a disinfection status from a disinfection device; 2) receiving and identification of the needleless connector; 3) sending the disinfection status and the identification of the needleless connector to a remote computer system; and 4) storing the disinfection status and the identification of the needleless connector in an electronic medical record. The method further includes a step for receiving and identification of a patient associated with the needleless connector.

Some implementations of the present invention further include a method for monitoring and recording a disinfection event of a needleless connector, the method including steps for 1) attaching a disposable cleaning head to a rotor of a disinfection device; 2) using the disinfection device to record and identification of the needleless connector; 3) using the disinfection device to record an identification of a patient; 4) disinfecting the needleless connector; 5) recording completion of the disinfection of the needleless connector; and 6) updating an electronic medical record of the patient to include the disinfection event. The method further includes a step for tracking the disposable cleaning head to ensure that the disposable cleaning head is used for only one disinfection event. The method may further include steps for internally recording the disinfection event into a memory of the disinfection device; and linking the cleaning event to the identity of the patient.

BRIEF DESCRIPTION OF THE SEVERAL VIEWS OF THE DRAWINGS

In order that the manner in which the above-recited and other features and advantages of the invention are obtained will be readily understood, a more particular description of the invention briefly described above will be rendered by reference to specific embodiments thereof which are illustrated in the appended drawings. These drawings depict only typical embodiments of the invention and are not therefore to be considered to limit the scope of the invention.

DETAILED DESCRIPTION OF THE INVENTION

Figure 1:
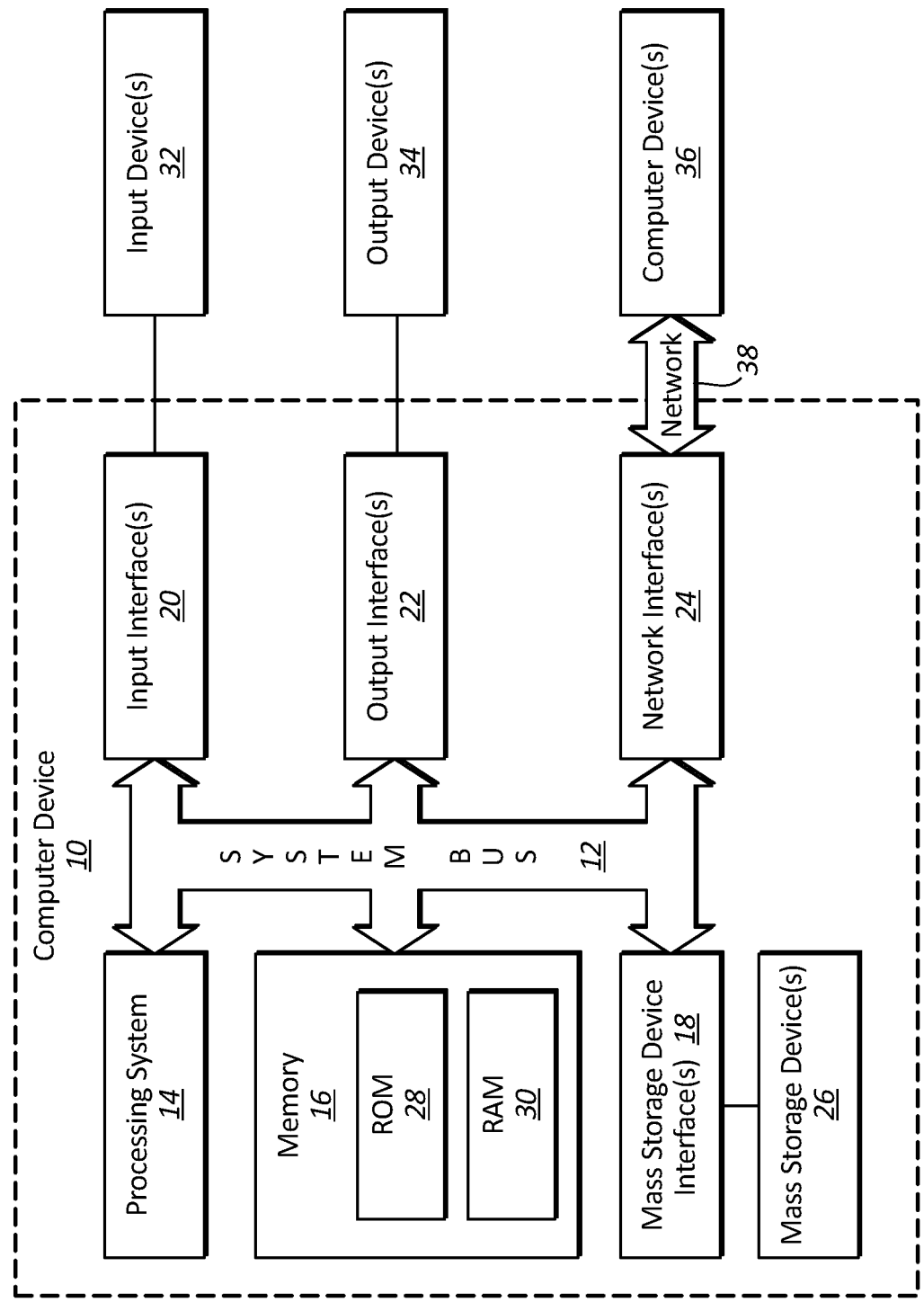
FIG. 1 shows a flow chart of a representative system that provides a suitable operating environment in which various embodiments of the present invention may be implemented.

The presently preferred embodiments of the present invention will be best understood by reference to the drawings, wherein like reference numbers indicate identical or functionally similar elements. It will be readily understood that the components of the present invention, as generally described and illustrated in the figures herein, could be arranged and designed in a wide variety of different configurations. Thus, the following more detailed description, as represented in the figures, is not intended to limit the scope of the invention as claimed, but is merely representative of presently preferred embodiments of the invention.

In general, the present invention relates to systems and methods for disinfecting a needleless connector. In particular, the present invention relates to a disinfection device comprising monitoring and feedback circuitry which monitors various minimum thresholds to ensure proper contact between a needleless connector and a cleaning head of the disinfection device. In some instances, a disinfection device further comprises a status indicator which communicates a status or level of disinfection of the needleless connector to a user.

As used herein, the term "threshold" is used to denote a minimum value, level, or point which is required to achieve sufficient disinfection of a needleless connector. In some instances, the term "threshold" is used to denote a minimum axial load needed to activate an axial load-sensitive switch. In other instances, the term "threshold" is used to denote a minimum pressure between a cleaning head of the disinfection device and a surface of a needleless connector. Further, in some instances the term "threshold" is used to denote a minimum length of time required to achieve disinfection of a needleless connector. Further still, in some instances the term "threshold" is used to denote a minimum rotational torque of a motor of a disinfection device. In other instances, the term "threshold" is used to denote a minimum length of time required to achieve a certain rotational speed of the motor.

As used herein, the term "disinfection" is used to denote a level of sanitation which is free from infection or free from microorganisms which are capable of promoting infection in the patient.

As used herein, the term "disinfectant" is used to denote an agent that destroys vegetative forms of harmful microorganisms such as bacteria, fungi, yeasts, viruses and other harmful pathogens.

As used herein, the term "needleless connector" is used to denote a medical coupler which is used as part of an intravenous assembly. In some instances, a needleless connector comprises a Luer adapter. In other instances, a needleless connector comprises a PRN connector. An example of a needleless connector is the Q-Syte™ luer access port from Becton, Dickinson. Further, in some instances a needleless connector comprises a port or valve of a section of intravenous tubing or a connector thereof. One having skill in the art will appreciate that the systems and methods of the present invention may be adapted for use with various other types of connectors and other devices for which automated disinfection is desirable.

As used herein, the term "disinfection event" denotes a process by which a disinfection device is used to disinfect a needleless connector, in accordance with the teachings of the present invention. In some instances, a disinfection event is preceded by collecting information regarding the patient and/or the needleless connector via an input interface of the disinfection device. The identifying information may be temporarily stored within memory of the disinfection device for later transmission to a remote computer device, or may be transferred to a remote computer device in real-time.

Figure 2:
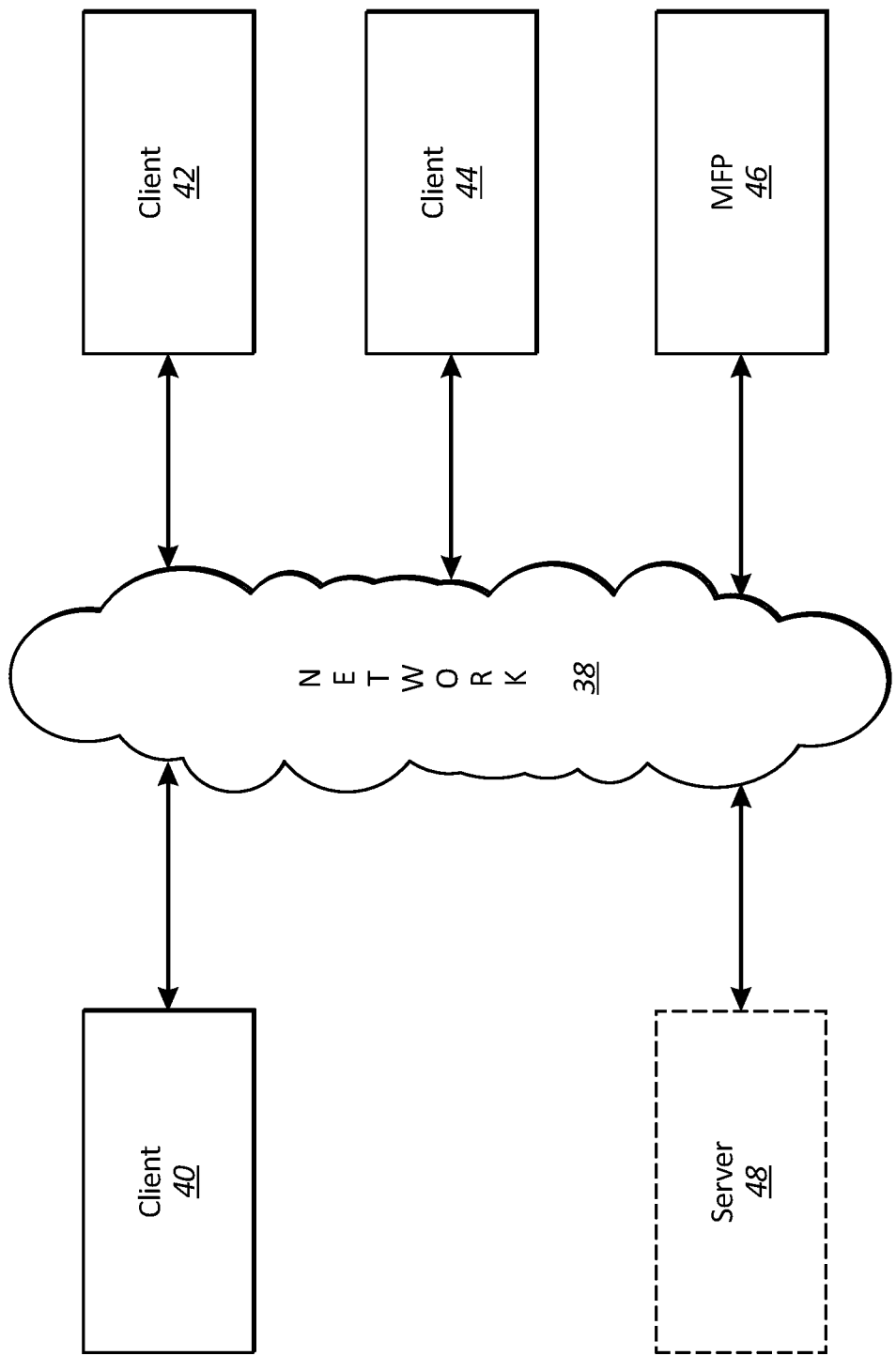
FIG. 2 shows a flow chart of a representative networking system that provides a suitable environment in which various embodiments of the present invention may be implemented.

FIGS. 1 and 2, and the corresponding discussion, provide a general description of a suitable operating environment in which embodiments of the invention may be implemented. One skilled in the art will appreciate that embodiments of the invention may be practiced by one or more computing devices and in a variety of system configurations, including in a networked configuration. However, while the methods and processes of the present invention have proven to be particularly useful in association with a system comprising a general purpose computer, embodiments of the present invention include utilization of the methods and processes in a variety of environments, including embedded systems with general purpose processing units, digital/media signal processors (DSP/MSP), application specific integrated circuits (ASIC), stand alone electronic devices, and other such electronic environments.

Embodiments of the present invention embrace one or more computer readable media, wherein each medium may be configured to include or includes thereon data or computer executable instructions for manipulating data. The computer executable instructions include data structures, objects, programs, routines, or other program modules that may be accessed by a processing system, such as one associated with a general-purpose computer capable of performing various different functions or one associated with a special-purpose computer capable of performing a limited number of functions. Computer executable instructions cause the processing system to perform a particular function or group of functions and are examples of program code means for implementing steps for methods disclosed herein. Furthermore, a particular sequence of the executable instructions provides an example of corresponding acts that may be used to implement such steps. Examples of computer readable media include random-access memory ("RAM"), read-only memory ("ROM"), programmable read-only memory ("PROM"), erasable programmable read-only memory ("EPROM"), electrically erasable programmable read-only memory ("EEPROM"), compact disk read-only memory ("CD-ROM"), or any other device or component that is capable of providing data or executable instructions that may be accessed by a processing system.

With reference to FIG. 1, a representative system for implementing embodiments of the invention includes computer device 10, which may be a general-purpose or special-purpose computer. For example, computer device 10 may be a personal computer, a notebook computer, a personal digital assistant ("PDA") or other hand-held device, a workstation, a minicomputer, a mainframe, a supercomputer, a multi-processor system, a network computer, a processor-based consumer electronic device, a smart phone, a position identifier, a ball collector, or the like.

Computer device 10 may include a system bus 12, which may be configured to connect various components thereof and enables data to be exchanged between two or more components. System bus 12 may include one of a variety of bus structures including a memory bus or memory controller, a peripheral bus, or a local bus that uses any of a variety of bus architectures. Typical components connected by system bus 12 include processing system 14 and memory 16. Other components may include one or more mass storage device interfaces 18, input interfaces 20, output interfaces 22, and/or network interfaces 24, each of which will be discussed below.

Processing system 14 includes one or more processors, such as a central processor and optionally one or more other processors designed to perform a particular function or task. It is typically processing system 14 that executes the instructions provided on computer readable media, such as on memory 16, a magnetic hard disk, a removable magnetic disk, a magnetic cassette, an optical disk, thumb drives, solid state memory, a universal serial bus or from a communication connection, which may also be viewed as a computer readable medium.

Memory 16 includes one or more computer readable media that may be configured to include or includes thereon data or instructions for manipulating data, and may be accessed by processing system 14 through system bus 12. Memory 16 may include, for example, ROM 28, used to permanently store information, and/or RAM 30, used to temporarily store information. ROM 28 may include a basic input/output system ("BIOS") having one or more routines that are used to establish communication, such as during start-up of computer device 10. RAM 30 may include one or more program modules, such as one or more operating systems, application programs, and/or program data.

One or more mass storage device interfaces 18 may be used to connect one or more mass storage devices 26 to system bus 12. The mass storage devices 26 may be incorporated into or may be peripheral to computer device 10 and allow computer device 10 to retain large amounts of data. Optionally, one or more of the mass storage devices 26 may be removable from computer device 10. Examples of mass storage devices include hard disk drives, magnetic disk drives, thumb drive tape drives and optical disk drives. A mass storage device 26 may read from and/or write to a magnetic hard disk, a removable magnetic disk, a magnetic cassette, an optical disk, or another computer readable medium. Mass storage devices 26 and their corresponding computer readable media provide nonvolatile storage of data and/or executable instructions that may include one or more program modules such as an operating system, one or more application programs, other program modules, or program data. Such executable instructions are examples of program code means for implementing steps for methods disclosed herein.

One or more input interfaces 20 may be employed to enable a user to enter data and/or instructions to computer device 10 through one or more corresponding input devices 32. Examples of such input devices include a keyboard and alternate input devices, such as a mouse, trackball, light pen, stylus, or other pointing device, a microphone, a joystick, a game pad, a satellite dish, a scanner, a camcorder, a digital camera, and the like. Similarly, examples of input interfaces 20 that may be used to connect the input devices 32 to the system bus 12 include a serial port, a parallel port, a game port, a universal serial bus ("USB"), an integrated circuit, a firewire (IEEE 1394), or another interface. For example, in some embodiments input interface 20 includes an application specific integrated circuit (ASIC) that is designed for a particular application. In a further embodiment, the ASIC is embedded and connects existing circuit building blocks.

One or more output interfaces 22 may be employed to connect one or more corresponding output devices 34 to system bus 12. Examples of output devices include a monitor or display screen, a speaker, a printer, a multi-functional peripheral, and the like. A particular output device 34 may be integrated with or peripheral to computer device 10. Examples of output interfaces include a video adapter, an audio adapter, a parallel port, and the like.

One or more network interfaces 24 enable computer device 10 to exchange information with one or more other local or remote computer devices, illustrated as computer devices 36, via a network 38 that may include hardwired and/or wireless links. Examples of network interfaces include a network adapter for connection to a local area network ("LAN") or a modem, wireless link, or other adapter for connection to a wide area network ("WAN"), such as the Internet. The network interface 24 may be incorporated with or peripheral to computer device 10. In a networked system, accessible program modules or portions thereof may be stored in a remote memory storage device. Furthermore, in a networked system computer device 10 may participate in a distributed computing environment, where functions or tasks are performed by a plurality of networked computer devices.

Thus, while those skilled in the art will appreciate that embodiments of the present invention may be practiced in a variety of different environments with many types of system configurations, FIG. 2 provides a representative networked system configuration that may be used in association with embodiments of the present invention. The representative system of FIG. 2 includes a computer device, illustrated as client 40, which is connected to one or more other computer devices (illustrated as client 42 and client 44) and one or more peripheral devices (illustrated as multifunctional peripheral (MFP) MFP 46) across network 38. While FIG. 2 illustrates an embodiment that includes a client 40, two additional clients, client 42 and client 44, one peripheral device, MFP 46, and optionally a server 48, connected to network 38, alternative embodiments include more or fewer clients, more than one peripheral device, no peripheral devices, no server 48, and/or more than one server 48 connected to network 38. Other embodiments of the present invention include local, networked, or peer-to-peer environments where one or more computer devices may be connected to one or more local or remote peripheral devices. Moreover, embodiments in accordance with the present invention also embrace a single electronic consumer device, wireless networked environments, and/or wide area networked environments, such as the Internet.

Figure 3:
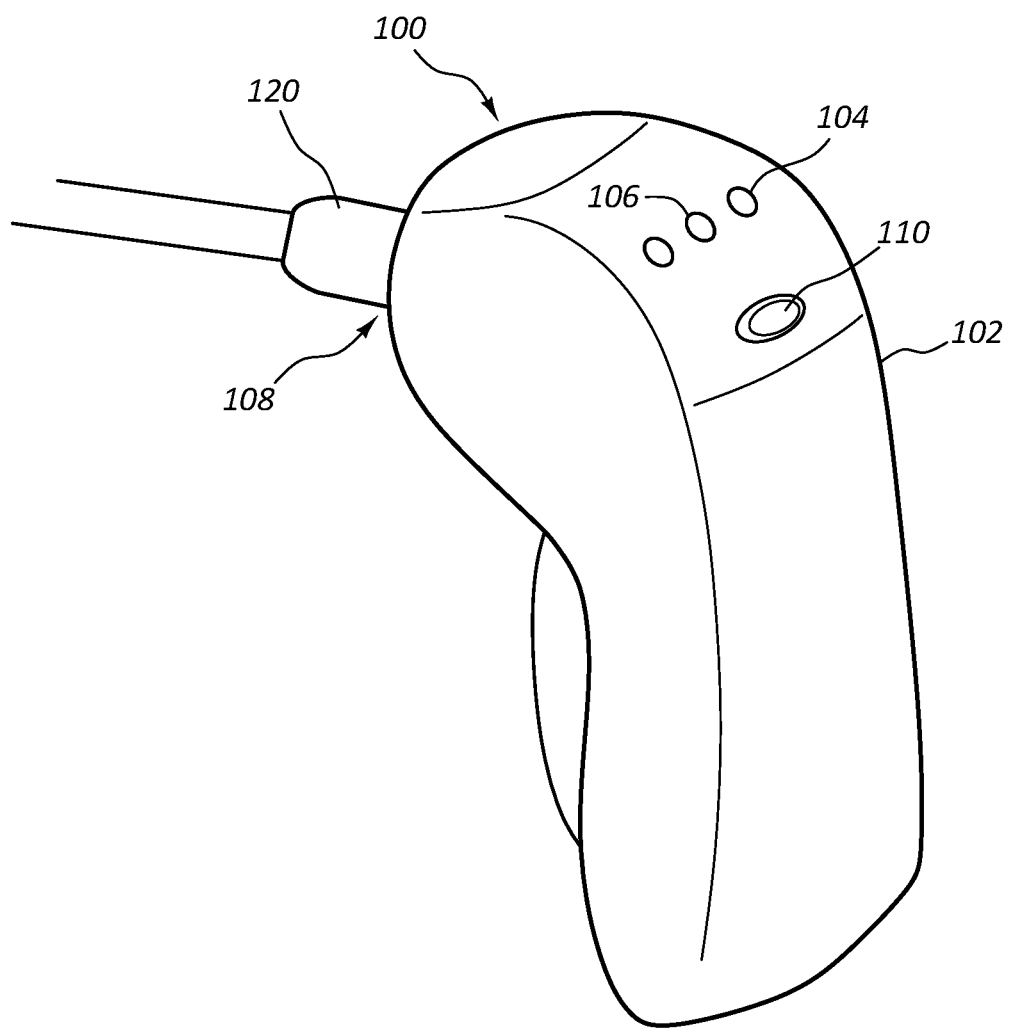
FIG. 3 is a perspective view of a handheld disinfection device in accordance with a representative embodiment of the present invention.

Referring now to FIG. 3, an implementation of a disinfection device 100 is shown. In some embodiments, a disinfection device 100 is provided as a handheld unit, wherein the disinfection device comprises a housing 102 which is sized and configured to be held in the hand of the user during disinfection of a needleless connector 120. Housing 102 of disinfection device 100 may include any size, shape and/or configuration as may be desirable. For example, in some embodiments disinfection device 100 comprises a stationary tabletop unit.

In some embodiments, housing 102 of disinfection device 100 further comprises one or more status indicators 104 which indicate a level of disinfection of needleless connector 120. For example, in some instances status indicators 104 comprise one or more lights 106 which are configured to provide information to a user. In some instances, lights 106 may blink to indicate a stage or level of disinfection for needleless connector 120. Lights 106 may further comprise two or more colors, wherein a color indicates a stage or level of disinfection for needleless connector 120. For example, in some embodiments a red light indicates incomplete or unsatisfactory disinfection of needleless connector 120. Further, a yellow light may indicate an intermediary or active process of disinfection for needleless connector 120. Further still, a green light may indicate a satisfactory or complete disinfection for needleless connector 120. In some instances, the indicators can be at least one of the LED screen with text, symbols, instruction, animation with both visual and audible alert including tone, buzz, and or speech.

Lights 106 may further be programmed to blink or otherwise demonstrates a lighted pattern to further communicate a status of disinfection device 100. For example, in some embodiments lights 106 may be programmed to demonstrate a lighted pattern to indicate a low battery. Lights 106 may further be programmed to demonstrate an error or mechanical malfunction. In some instances, lights 106 may be programmed to indicate that disinfection device 100 is ready to receive needleless connector 120.

In some embodiments, disinfection device 100 comprises a cleaning head 108 which is positioned on housing 102 at a location which facilitates easy access for needleless connector 120. In some instances, cleaning head 108 is positioned opposite of status indicators 104 thereby permitting the user to access cleaning head 108 with needleless connector 120 while maintaining visualization a status indicators 104. Cleaning head 108 may be accessed as a user holds disinfection device 100 in their hand 110 while aligning and contacting needleless connector 120 with cleaning head 108 using the user's other hand 112. Following disinfection, the user removes needleless connector 120 from cleaning head 108 thereby completing the disinfection process.

Figure 4:
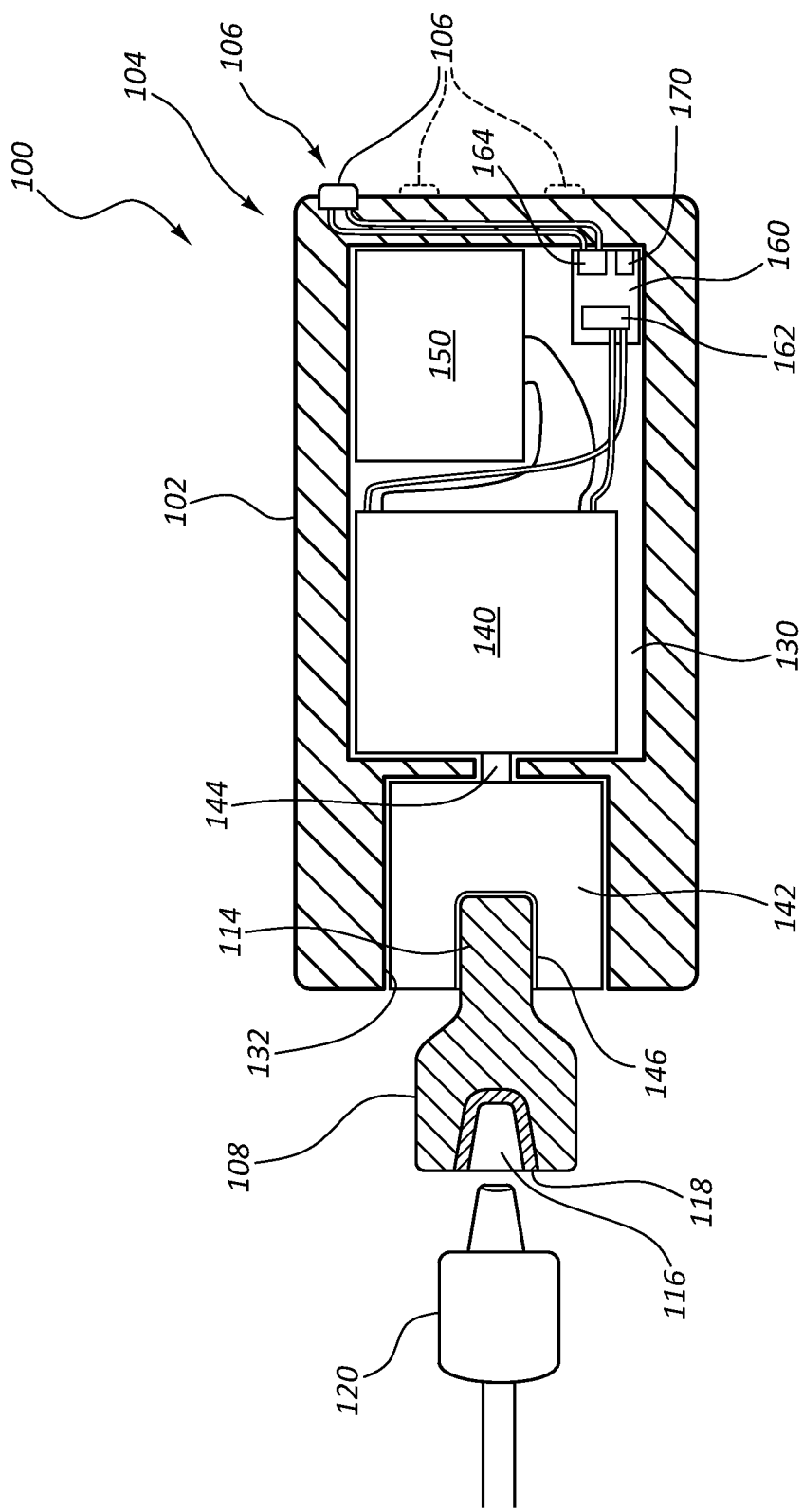
FIG. 4 is a cross-section top view of the handheld disinfection device shown in FIG. 3 in accordance with a representative embodiment of the present invention.

Referring now to FIG. 4, a cross-section top view of disinfection device 100 is shown. In some embodiments, housing 102 comprises an interior 130 in which is housed various components of the device. For example, interior 130 houses a motor 140 which is rotatably connected to a rotor 142 via a motor shaft 144. Rotor 142 is positioned within a distal opening 132 of housing 102 such that a socket or receptacle 146 is accessible to the user. Receptacle 146 is sized and configured to compatibly receive and retain a post portion 114 of cleaning head 108. In some embodiments, cleaning head 108 is disposable. In other embodiments, cleaning head 108 is reusable. In other embodiment, the cleaning head can be one of the commercially available disinfecting head or cap. Cleaning head 108 further comprises an opening 116 having a length and diameter to compatibly receive needleless connector 120. Opening 116 further comprises a cleaning pad 118 which may be soaked or otherwise preloaded with a cleaning agent or disinfectant. In some instances, a disinfectant is loaded onto cleaning pad 118 prior to introducing needleless adapter 120 into opening 116.

Motor 140 is generally provided as a means for rotating rotor 142 about a central axis defined by motor shaft 144. In some instances, disinfection device 100 further comprises a speed control (not shown) whereby to regulate the speed at which motor 140 rotates rotor 142. In other instances, the speed at which rotor 142 rotates is affected by a friction between needleless connector 120 and cleaning pad 118. Some implementations of the present invention further comprise an electronic speed control (not shown) which controls the rotational speed of rotor 142 such that rotor 142 rotates at a constant speed regardless of friction between needleless connector 120 and cleaning pad 118.

Motor 140 may comprise any type or size of motor compatible with various embodiments of the present invention. For example, in some instances motor 140 comprises a DC motor which is powered by an internal battery 150. In other instances, motor 140 comprises an AC motor which is powered by an external power source (not shown). Motor 140 may further include a unidirectional rotation motion, a bidirectional rotation motion, or an oscillatory rotation motion.

Disinfection device 100 may further comprise a printed circuit board 160 which comprises various monitoring and feedback circuitry to control proper disinfection of needleless connector 120. For example, in some embodiments printed circuit board 160 comprises a speed sensor 162 which is configured to monitor and measure the rotational speed of rotor 142. Printed circuit board 160 may further comprise a status indicator controller 170 Speed sensor 162 monitors and measures the actual rotation speed of rotor 142 to determine whether a minimum axial rotation speed threshold is maintained by disinfection device 100 during disinfection of needleless connector 120.

Where speed sensor 162 measures an axial rotation speed for rotor 142 that is less than a minimum axial rotation speed, speed sensor 162 may generate an error code which is received by status indicator controller 164. Controller 164 may then send a signal to status indicator 104 which may cause light 106 to blink, display a color, or other lighted pattern to indicate insufficient axial rotation speed. In some instances, status indicator 104 comprises multiple lights (shown in phantom) to permit various combinations of light patterns and other signals or LCD screens that provide picture, text, animation, and audible feedback. Where a minimum axial rotation speed threshold is known, axial rotation speeds that are less than the minimum axial rotation speed threshold provide insufficient disinfection for needleless connector 120. Accordingly, a user may be required to lessen friction between needleless connector 120 and cleaning head 108 to permit a minimally acceptable axial rotation speed.

In some embodiments, another sensor 164 measures the actual rotational torque of rotor 142 and/or motor shaft 144. The disinfection action of the present invention involves friction contact between needleless connection 120 and cleaning pad 118. Such friction generates resistance to the rotational motion of motor 140, or torque loading on the motor. This torque load is proportional to the motor current required to rotate motor 140 at the minimum rotational speed threshold. Thus, in some embodiments sensor 164 measures rotational torque of rotor 142 by measuring the current of motor 140. As the load of motor 140 increases (such as by increasing friction between needleless connector 120 and cleaning head 108), so does the current of motor 140. In some instances, sensor 164 monitors the current of motor 140 to detect fluctuations in the current of motor 140 which may suggest a load that is prohibiting attainment of the minimum rotation speed threshold. Speed sensor 162 may then generate an error code for the user. In other instances, speed sensor 162 may allow additional amperage to motor 140 to compensate for an increased load, thereby maintaining the minimal axial rotation speed threshold for rotor 142. In yet other instance, the speed sensor 162 would increase the time the disinfection action is taking to ensure proper disinfection duration. Accordingly, some embodiments of the present invention provide a system that monitors the torque of motor 140 and sets a low threshold limit, thereby making it possible to guarantee proper engagement and/or pressure between cleaning head 108 and needleless connector 120, thus ensuring proper disinfection of connector 120.

In an alternative embodiment, an axial force on motor 140 may be measured with a load cell. Such force would correlate to the contact pressure between needleless connector 120 and cleaning head 108. A minimum threshold may thus be set on this axial force and monitored/reported by printed circuit board 160 and status indicator 104.

Printed circuit board 160 may further comprise a timer 170 whereby to measure a time lapse or interval over which the minimum rotation speed threshold is maintained by rotor 142. In some instances, sufficient disinfection is a factor of minimum rotation speed and time. For example, in some embodiments complete disinfection requires that the minimum axial rotation speed threshold be maintained for a minimal length of time, such as 15 seconds. Thus, timer 170 is configured to measure the length of time for which the minimum axial rotation speed threshold is maintained during disinfection of needleless connector 120. In some instanced, constant sustainment of the minimum axial rotation speed threshold is required for a determined length of time. In other instance, intermittent sustainment of the minimum axial rotation speed threshold for a cumulative length of time is sufficient for complete disinfection. Thus, timer 170 may be configured to measure axial rotation and time as may be determined to achieve complete disinfection.

In some embodiments, the timer 170 is used to also monitor the time for the motor to reach certain minimum rotational speed. Since the proper contact between the needleless connector and the cleaning head would generate certain friction, the time it takes for the motor to reach certain rotational speed will be increase comparing to the cases where the needleless connector is absent. Making sure the time to reach certain rotational speed is greater than a minimum value would ensure proper engagement and disinfection of the needleless connector. This approach could be used preferably when oscillatory rotational cleaning motion is used.

Figure 5:
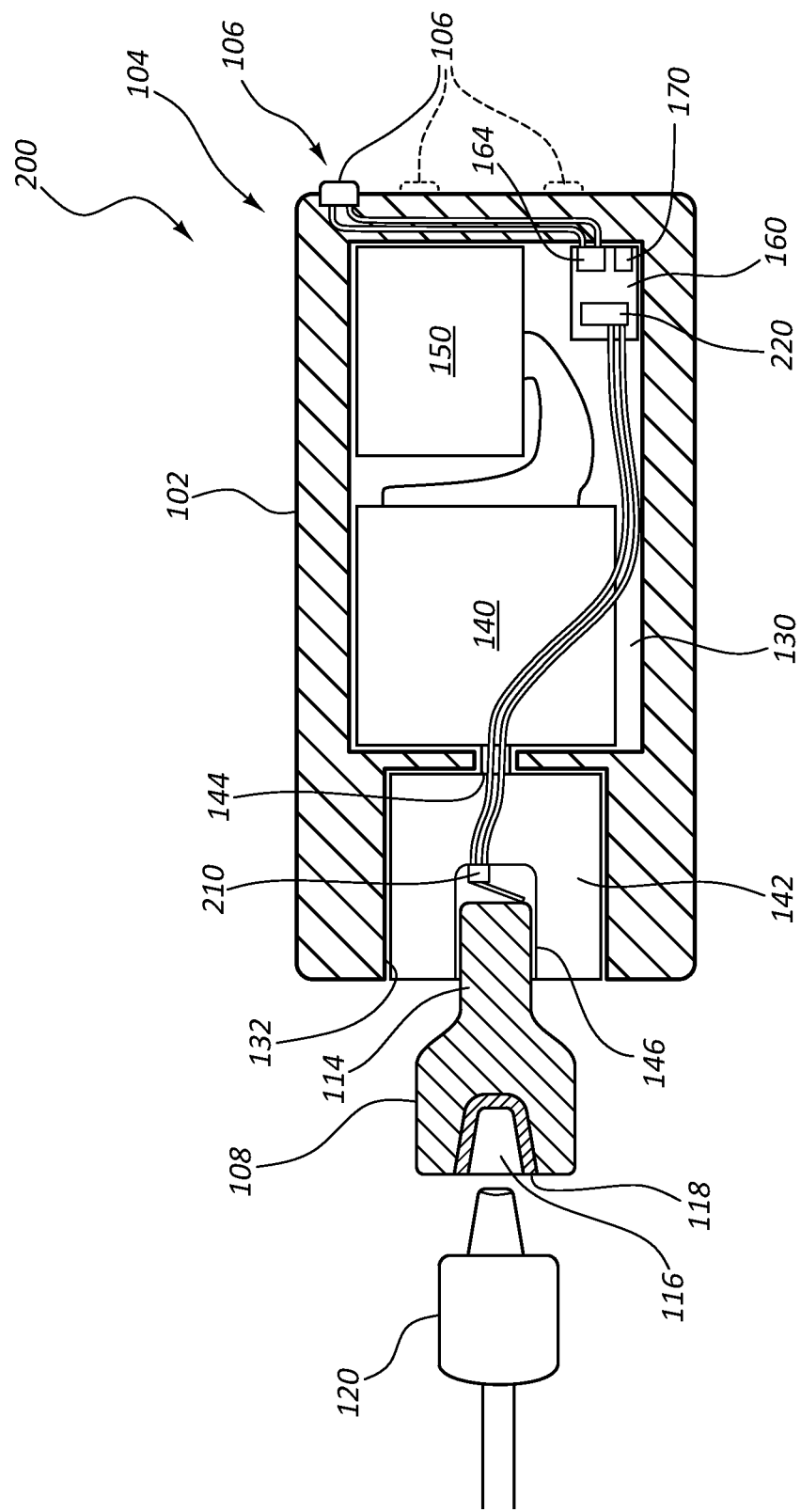
FIG. 5 is a cross-section top view of a disinfection device in accordance with a representative embodiment of the present invention.
Figure 5A:
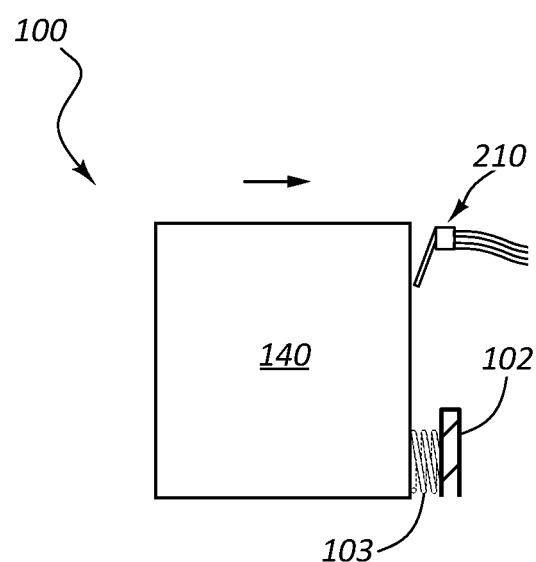
FIG. 5A is a partial cross-section view of a disinfection device in accordance with the representative embodiment of the present invention.

Referring now to FIG. 5, in some embodiments disinfection device 200 further comprises a pressure-sensitive switch 210 which is interposedly positioned between post 114 of cleaning head 108 and receptacle 146. Switch 210 may be positioned at any location within disinfection device 200 or cleaning head 108 which is capable of measuring a contact pressure between needleless connector 120 and cleaning pad 118. For example, device 100 may comprise a spring 103 on which motor 140 is mounted (as shown in FIG. 5A), wherein upon establishing contact between cleaning head 108 and connector 120, the spring is compressed thereby engaging a switch which completes a circuit between motor 140 and battery 150 to cause motor 140 to rotate.

Switch 210 is provided to measure pressure between needleless connector 120 and cleaning pad 118. Some embodiments of the present invention comprises a known minimum pressure which must be attained between needleless connector 120 and cleaning pad 118 to achieve complete disinfection. Accordingly, switch 210 measures pressure between connection 120 and pad 118 by measuring pressure between post 114 and switch 210. Upon initial contact between connector 120 and cleaning pad 118, pressure-sensitive switch 210 is activated thereby causing motor 140 to rotate rotor 142 and cleaning head 108. As contact pressure between connection 120 and pad 118 increases and exceeds a minimum pressure threshold, switch 210 signals pressure sensor 220 that the minimum threshold has been reached. In some instances, timer 170 monitors the length of time over which the minimum threshold is maintained. Following sufficient disinfection, signal indicator 104 provides a signal to the user indicating that complete disinfection has been attained.

Figure 6:
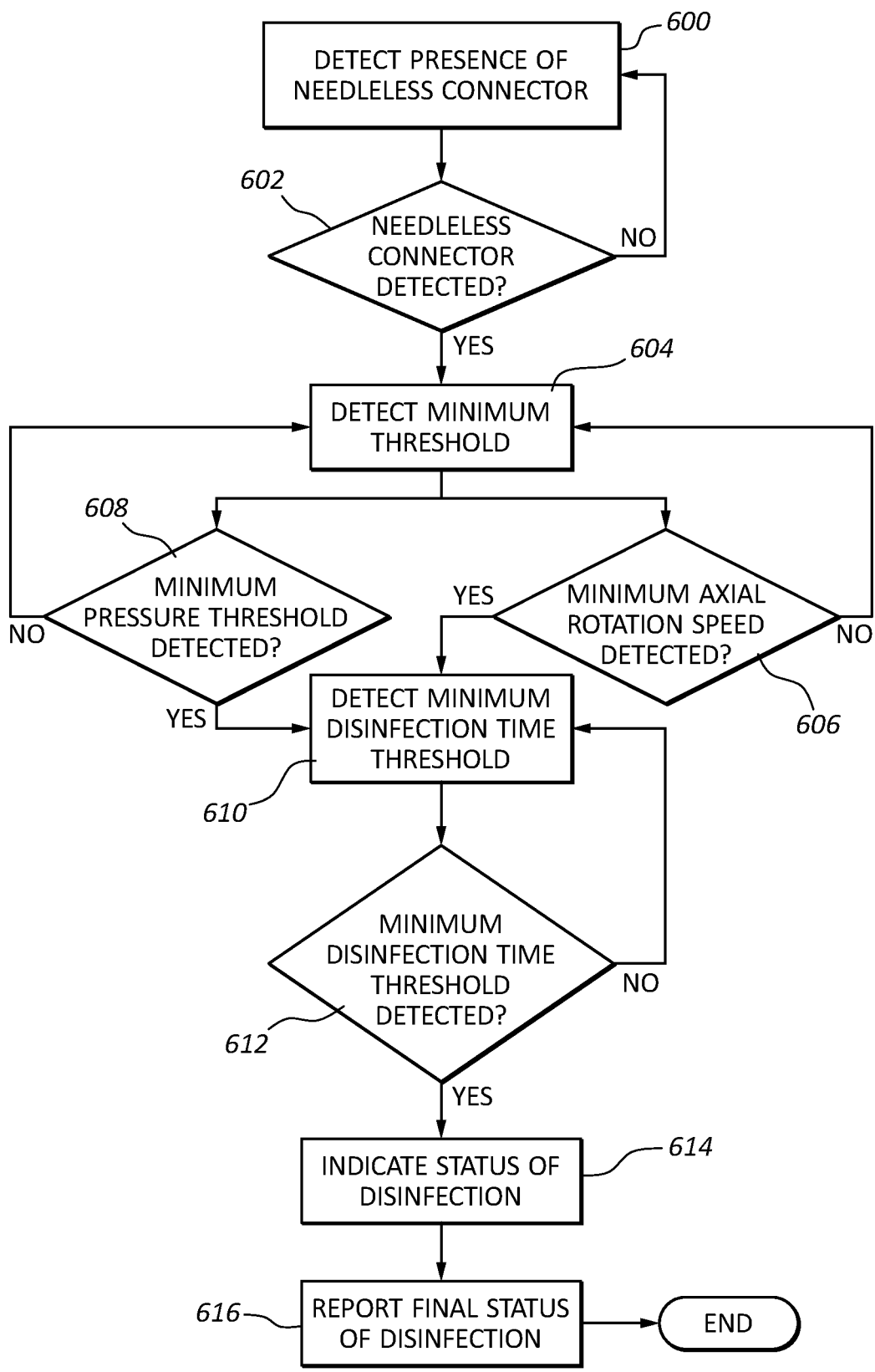
FIG. 6 is a flowchart demonstrating a method for controlling proper disinfection of a needleless connector in accordance with a representative embodiment of the present invention.

Referring now to FIG. 6, a flowchart for a computer software program in accordance with a representative embodiment of the present invention is shown. In some embodiments, a computer software program is provided having computer executable instructions to detect the presence of a needleless connector (at step 600). As discussed above, the disinfection device may be provided having hardware that attacks the physical presence of a needleless connector, such as a pressure-sensitive switch. Some embodiments of the present invention further comprise a disinfection device having a light sensor or other type of sensor which is configured to detect the presence of needleless connector in contact with a cleaning head of the device.

Once a needleless connector is detected (at step 602), the computer executable instructions then detect a minimum threshold of the disinfection device (at step 604). As discussed previously, a minimum threshold may include a minimum pressure (at step 608), a minimum axial rotation speed (at step 606), a minimum disinfection time interval (at step 610), a combination of one or more minimum thresholds, or other minimum thresholds which are determined to achieve sufficient or complete disinfection of a needleless connector.

Once complete disinfection of a needleless connector is detected (at step 612), the computer executable instructions then indicate a status of disinfection (at step 614). As discussed previously, the step of indicating a status of disinfection may be executed at any stage of the disinfection process. For example, in some embodiments a status of disinfection is provided to indicate completion of disinfection. In other embodiments, a status of disinfection is provided to indicate an incomplete disinfection. Further, in some embodiments a status of disinfection is provided to indicate a proper contact and/or pressure between a cleaning head of the disinfection device and a needleless connector. In some instances, the computer executable instructions further include a step for reporting a final status of disinfection (at step 616).

Figure 7:
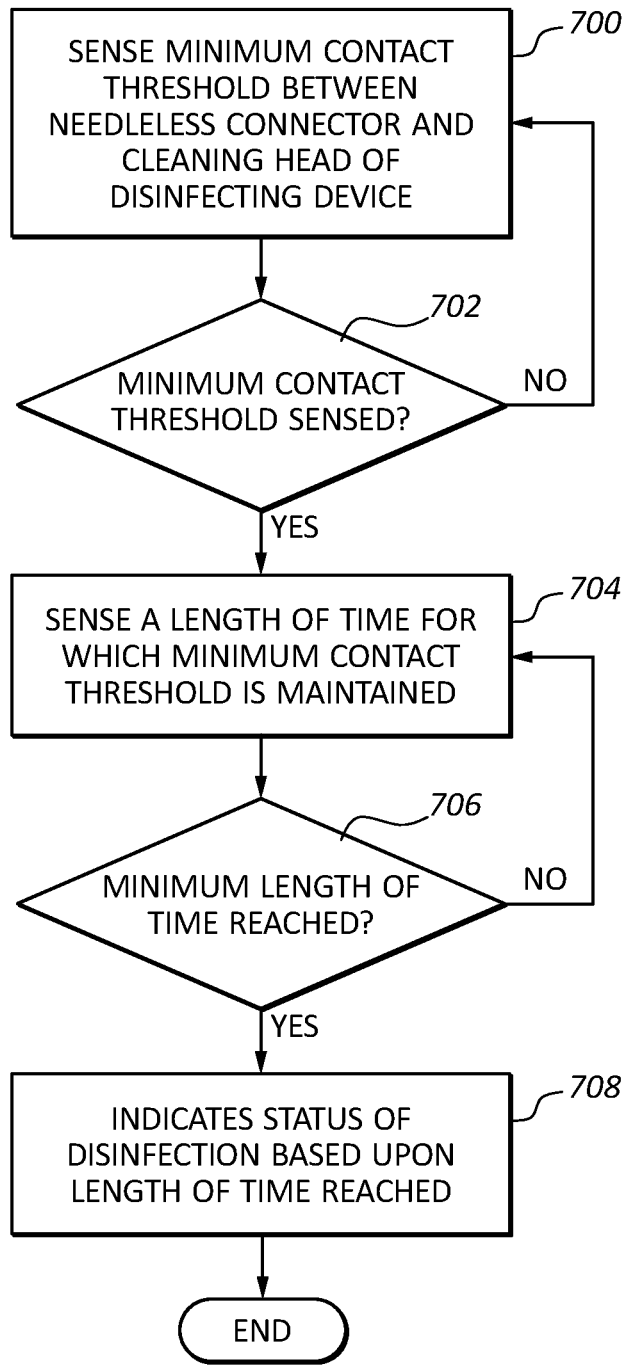
FIG. 7 is a flowchart demonstrating a method for controlling proper disinfection of a needleless connector in accordance with a representative embodiment of the present invention.

Referring now to FIG. 7, a method for controlling proper disinfection of a needleless connector in accordance with the present invention is shown. In some embodiments, a method comprises a first step of sensing a minimum contact threshold between a needleless connector and a cleaning head of a disinfection device (at step 700). A minimum contact threshold generally comprises a minimum pressure or minimum contact between the needleless connector and the cleaning head of the disinfection device, wherein the minimum contact threshold is determined to achieve or facilitate complete disinfection of the needleless connector. Upon sensing achievement of the minimum contact threshold (at step 702), a length of time for which the minimum contact threshold is maintained is further measured and/or sensed (at step 704). Some methods equate complete or sufficient disinfection based upon reaching a minimum length of time for which the minimum contact threshold is maintained. In some instances, the minimum length of time is 15 seconds. In other instances, the minimum length of time is greater than 15 seconds. Further still, in some instances the minimum length of time is less than 15 seconds.

Once the minimum length of time is reached, the status of disinfection is indicated, for example via a status indicator (at step 708). In some embodiments, a disinfection device is provided which is configured to automatically stop or turn off once complete or sufficient disinfection is achieved. In other embodiments, a disinfection device is configured to provide an audible signal to indicate complete disinfection. Systems may further include combinations of audible and visual signals to indicate a status of disinfection. Further still, systems may report a final status of disinfection.

Figure 8:
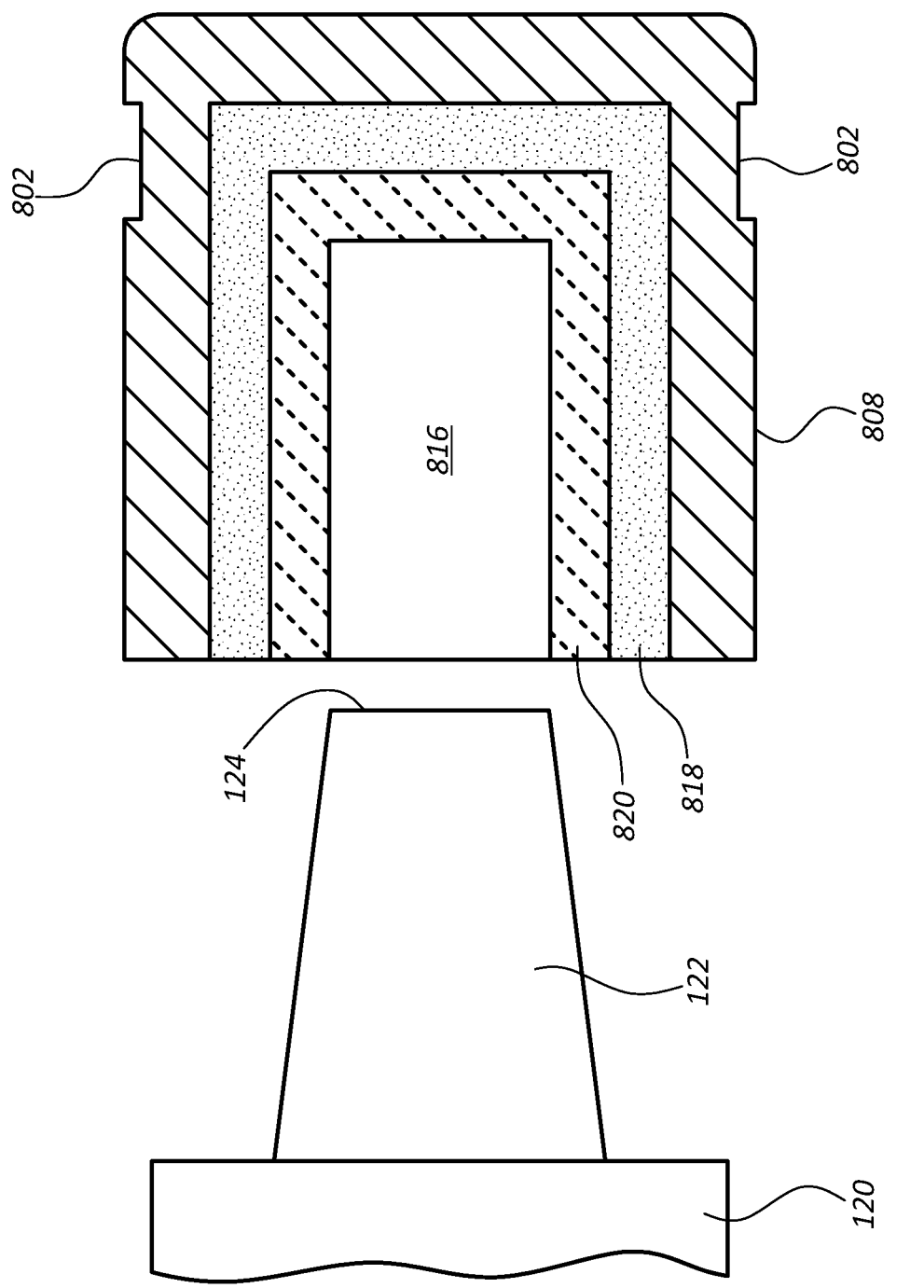
FIG. 8 is a cross-section view of a disinfection cleaning head and a needleless connector in accordance with a representative embodiment of the present invention.

The present invention may include various structures and features whereby to removably coupled the cleaning head to the rotor. For example, FIG. 8 illustrates an alternative embodiment of a cleaning head 808. Cleaning head 808 includes an inner chamber 816 that engages a portion 122 of needleless connector 120. A part of, or the entire inside surface of the inner chamber 816 can be lined with an absorbent material 818. Absorbent material 818 can include a porous foam material that exhibits compressible properties. Absorbent material 818 can be impregnated with a cleaning agent or disinfectant. Non-limiting examples of disinfectants include alcohol, iodine, and/or a chlorhexidine solution (e.g., a chlorhexidine gluconate (CHG) solution). In some embodiments, a pad or cloth 820 is coupled to the absorbent material 818. Cloth 820 or absorbent material 818 can interface with the needleless connector 120 during movement of the hub 142 to dispense the disinfectant on the needleless connector 120 and clean the surface of needleless connector 120. Cloth 820 or absorbent material 818 may be smooth or textured to effectively distribute disinfectant and/or provide cleaning action about needleless connector 120.

Cloth 820 or absorbent material 818 is configured to interface with needleless connector 120 when needleless connector 120 is inserted into cleaning head 808. This interaction may be facilitating by sizing the inner chamber 816 to be smaller than the outer dimensions of needleless connector 120. For instance, the diameter of inner chamber 116 may be smaller than the outer diameter of needleless connector 120 to allow cloth 820 or absorbent material 818 to contact all exterior side surfaces of needleless connector 120, including any threaded surfaces. Additionally, in some embodiments, the depth of inner chamber 816 may be shorter than the length of the needleless connector 120 to allow contact with all end surface of needleless connector 120. The smaller dimensions of inner chamber 816 can induce an inward pressure on needleless connector 120 and compress absorbent material 818. As absorbent material 818 is compressed, disinfectant impregnated within absorbent material 818 can migrate to the needleless connector 120. During operation of the disinfectant device 100, disinfectant in contact with the needleless connector 120 can be repeatedly swiped, scrubbed, and moved until it approximately covers all external surfaces of needleless connector 120. Exposure to the disinfectant along with the movement of the cleaning head 808 for a predetermined period of time can substantially disinfect the entire needleless connector 120.

In some embodiments, cleaning head 808 further includes one or more attachment features 802 that can be used to selectively couple cleaning head 808 to the hub 142. As shown, attachment features 802 can include an indent, an annular or partial recess or groove, or other depression that can be clasped or otherwise attached to the hub 142. Conversely, attachment features 802 can be a protrusion, latch, hook, or other such structure. In some embodiments, hub 142 can include a corresponding attachment feature configured to mate with and secure attachment features 802 of cleaning head 808, as shown in FIG. 9.

Figure 9:
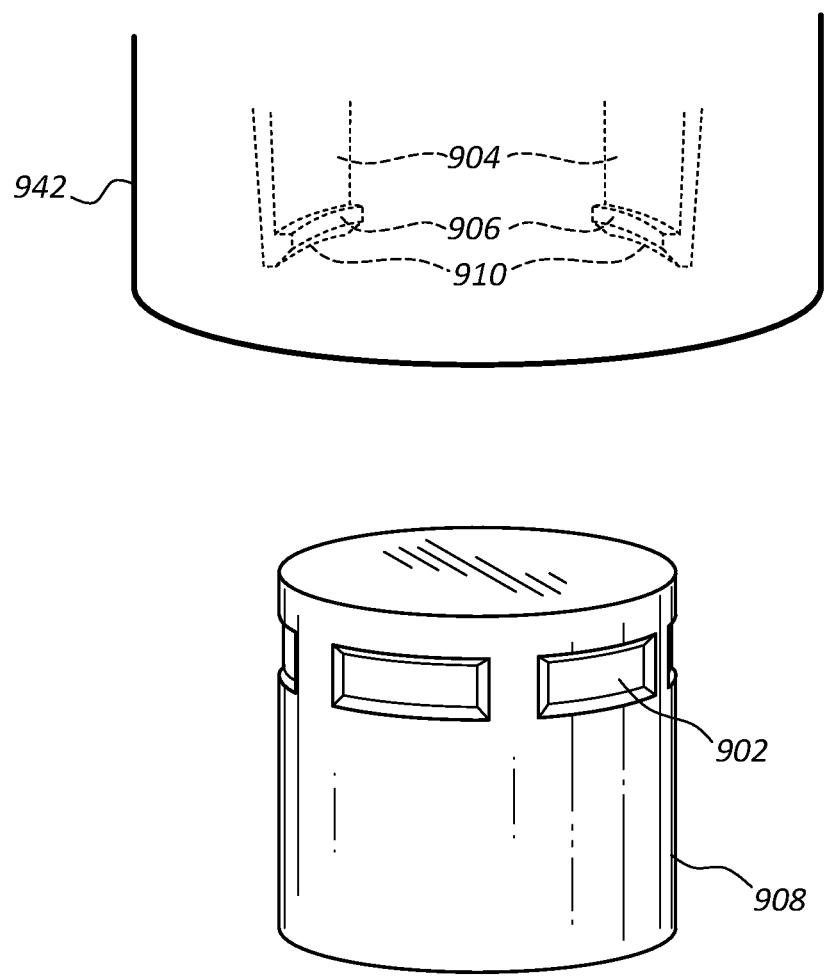
FIG. 9 is a perspective view of a representative cleaning head and hub receptacle having attachment arm shown in phantom in accordance with a representative embodiment of the present invention.

FIG. 9 illustrates representative embodiments of attachment features 902, 904 of a cleaning head 908, and a hub 942, respectively. As shown, in some embodiments, cleaning head 908 includes a series of indents 902 spaced radially about its exterior. Indents 902 can extend entirely through a wall or body of cleaning head 908 (e.g., windows in the cleaning head 308) or only partially into the wall or body (e.g., as a depression therein). Indents 902 can be configured to selectively interlock with a hook member 906 of an attachment arm 904 of hub 942. Attachment arms 904 can be coupled to the body of hub 942 and biased inwardly to apply an inward pressure against cleaning head 908. This pressure can secure cleaning head 908 in place and deter premature ejection of cleaning head 908 during high-speed rotation that may be experienced during disinfection operations. Any suitable number of indents 902 and corresponding attachment arms 904 can be utilized, including 2, 3, 4, 5, 6, 7, 8, 9, 10, 11, 12, or more than 12. Alternatively, a single annular indent (or groove) can replace the multiple indents 902.

In some embodiments, it may be advantageous to enable one-push attachment of cleaning head 908 into hub 942. Thus, an operating clinician can insert a new cleaning head 908 into receptacle 146 of hub 942 by merely inserting cleaning head 908 therein and applying enough pressure to interlock attachment arms 904 within indents 902. Accordingly, in some configurations, attachment arms can have inclined distal surfaces 910 that promote one-push snap-in attachments. Thus, as the proximal side of cleaning head 908 is pressed against inclined distal surfaces 910, the force on inclined distal surfaces 910 moves attachment arms 904 outward, permitting entry of cleaning head 908. As cleaning head 908 is advanced proximally, hook members 906 enter indents 902, latching cleaning head 908 within receptacle 146.

In some alternative embodiments, attachment arms 904 and indents 902 can be replaced with one or more magnets or electromagnets (not shown) that can attach and secure cleaning head 908 within receptacle 146. Non-limiting examples of magnets include rare earth magnets. When configured with one or more electromagnets, cleaning head 908 can be ejected or attached detached by switching the electromagnet off and on, respectively. One or more switches can be provided to toggle the electromagnet power.

Figure 10:
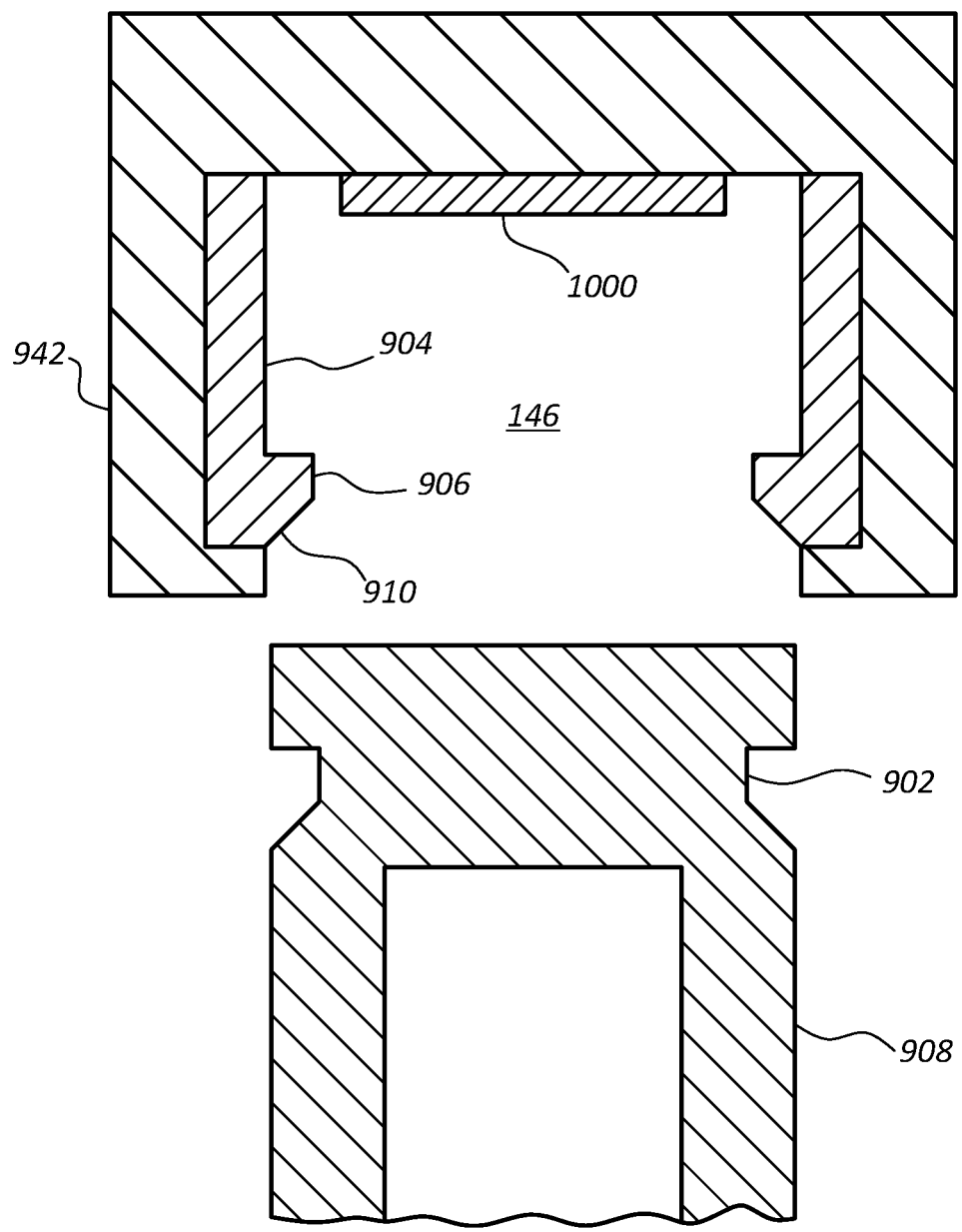
FIG. 10 is a cross-section view of a cleaning head and hub receptacle, prior to insertion of the cleaning head, in accordance with a representative embodiment of the present invention.
Figure 12:
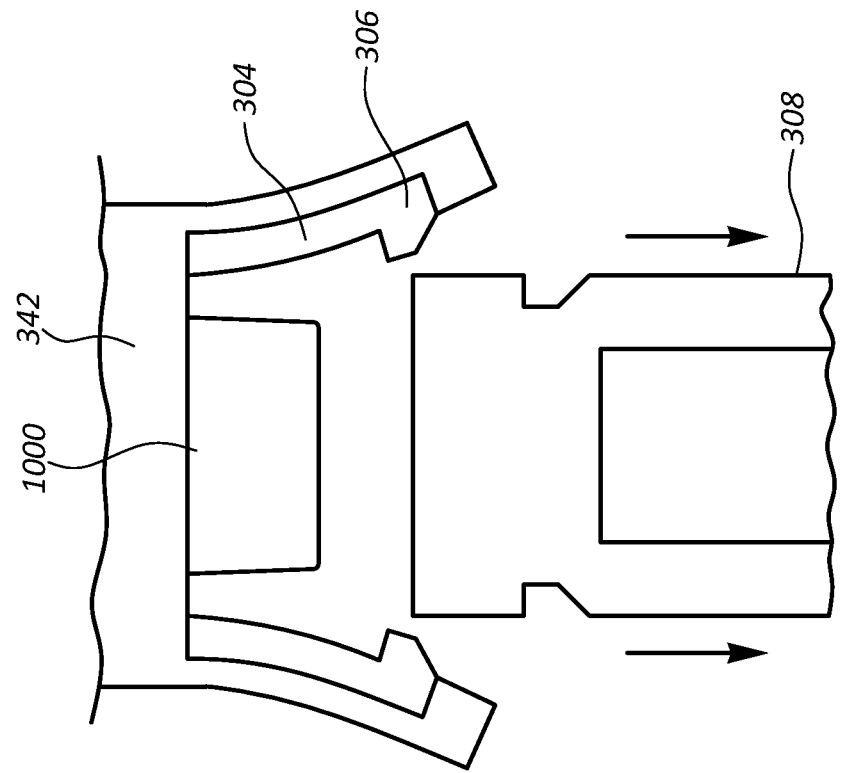
FIG. 12 is a cross section view of a cleaning head and hub receptacle, after ejection of the cleaning head, in accordance with a representative embodiment of the present invention.
Figure 11:
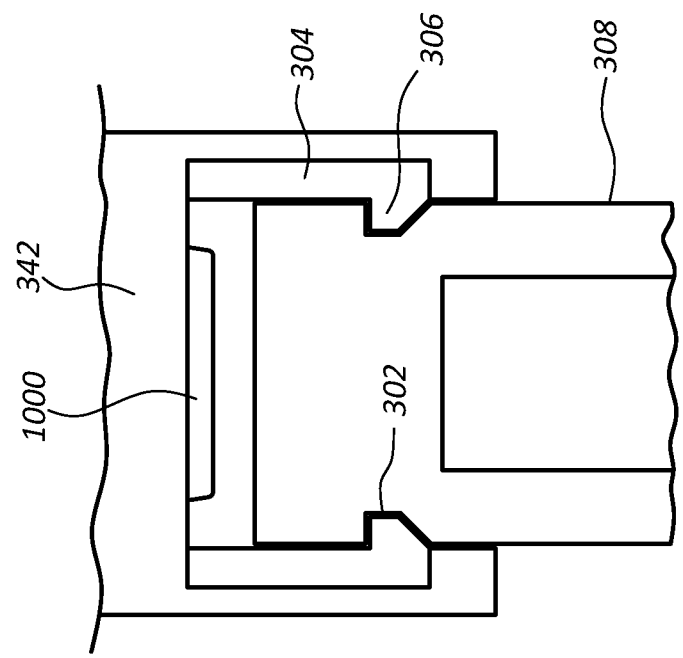
FIG. 11 is a cross section view of a cleaning head and hub receptacle, after insertion of the cleaning head, in accordance with a representative embodiment of the present invention.

Reference will now be made to FIGS. 10 through 12, which illustrate the process of attaching and detaching cleaning head 908 to hub 942. Turning first to FIG. 10, cleaning head 908 and receptacle 146 having attachment arms 904 similar to those of FIG. 9 are depicted. As mentioned, due to the inclined orientation of the proximal end of attachment arms 904, cleaning head 908 may be inserted within receptacle 146 by applying a threshold proximal force thereto. Once cleaning head 908 is proximally advanced to the point at which hook members 906 of attachment arms 904 insert within indents 902, the cleaning head 908 is secured and prepared for disinfecting operation, as shown in FIG. 11.

After one or more disinfecting operation, cleaning head 908 may be ejected. When detached, cleaning head may remain on a needleless connector to act as a physical contamination barrier or disposed of in the trash. In either case, an operating clinician may not be required to contact cleaning head 908, which has been used at this point. Rather, in some configurations, the clinician may simply eject cleaning head 908 using an ejection button, such as button 110 of FIG. 3.

In some embodiments, as shown in FIGS. 10 and 12, an ejector 1000 is disposed within a proximal end of receptacle 146. Ejector 1000 may be a piston or other movable structure that can selectively press distally against cleaning head 908 until it is forced out receptacle 146. The distal force of ejector 1000 can cause attachment arms 904 and/or hub 942 to flex outwardly away from cleaning head 908. As this force is sufficiently increased, hook members 906 of attachment arms 904 are released from within indents 902 of cleaning head 908, freeing cleaning head 908 to be ejected from receptacle 146. In some embodiments which utilize magnetic attachment means, cleaning head 908 may similarly be ejected using a manual ejector 1000 or by simply turning off power to an electromagnet.

From the foregoing, it will be seen that the present disinfecting device can disinfect a needleless connector. When a needleless connector is at least partially inserted within the cleaning head of the disinfecting device, disinfectant within the cleaning head may be applied to the exterior surfaces of the needleless connector, preparing it for use. Moreover, a detachable cleaning head can couple to a needleless connector after it is detached from the disinfection device to protect the needleless connector until it is used.

Figure 13:
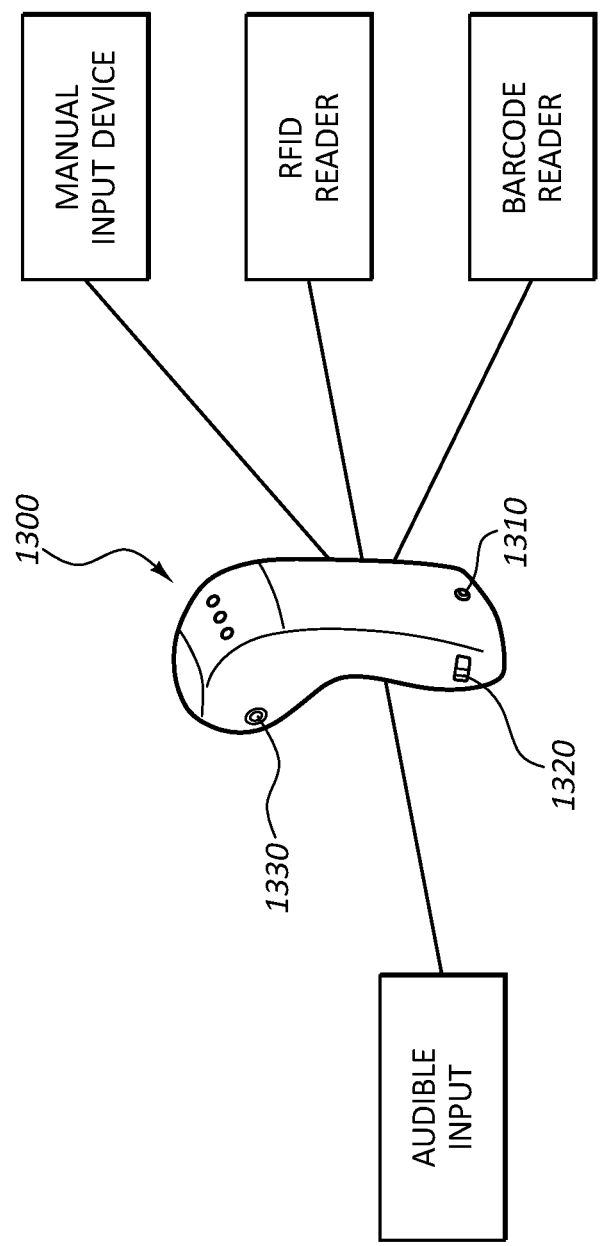
FIG. 13 is a perspective view of a handheld disinfection device further comprising input and output features in accordance with a representative embodiment of the present invention.

Referring now to FIG. 13, an implementation of a disinfection device 1300 is shown. Disinfection device 1300 is similar to disinfection device 100, however disinfection device 1300 further comprises an input interface 1310 and an output interface 1320 to facilitate collection and reporting of information related to a cleaning event of disinfection device 1300. For example, in some embodiments input interface 1310 comprises a barcode scanner which is capable of reading a computer-readable barcode that is placed on needleless connector 120, and/or an identification tag or label of the patient. In other embodiments, input interface 1310 further comprises a magnetic card reader, or an optical camera which is capable of retrieving information stored within a magnetic stripe or a computer-readable code, respectively. For example, a patient may have an identification card having a magnetic stripe which contains the identity of the patient and other related medical information. The patient and/or needleless connector may further include a QR code which is capable of being detected and deciphered using an optical camera and computer-executable software configured to retrieve information from the QR code. In other embodiments, the patient and/or needleless connector may further include an RFID tag which can be read by a RFID reader on the disinfection device.

Some embodiments of the present invention further comprise a device or component of a device that includes a material, a coating, or a tag containing a material or coating that is configured to change color in response to prolonged exposure to air and/or a liquid. A color-changing material may be useful in communicating to a user a length of time for which the cleaning head and/or needleless connector has been exposed to an unsterile environment. A color-changing material may also be useful in communicating to a user that the device or component has been previously used. In some instances, a device or component of the present invention is packaged in airtight packaging, thereby preserving an initial color of the color-changing material. Upon opening the airtight packaging, the color-changing material is exposed to air thereby changing the color of the device or component. This feature may prevent a device or component from being reused. This feature may also prevent an unsterile device or component from being used.

In some embodiments, information relating to the identity of the patient and the identity of the needleless adapter are retrieved and stored by input interface 1310 prior to a disinfection event. In some instances, additional information relating to the disinfection event is further collected and stored in memory of the disinfection device. For example, disinfection device 1300 may further collect and store information such as the date and time of the disinfection event, the identity of the clinician, and a final disinfection status of the needleless connector. Following the disinfection event, the collected and stored information is transferred to a remote computer device via output interface 1320.

Similarly, the information related to the identity of the cleaning head can be retrieved and stored by the input interface 1310. The collection of the information on the identity of the cleaning head can be particularly important where the cleaning head is to be used only once. The disinfection action can be prevented if the cleaning head has been used previously.

Output interface 1320 may include any type or configuration of output which is capable of transferring stored information from disinfection device 1300 to a remote computer device. For example, in some embodiments output interface 1320 comprises a wireless antenna. In other embodiments, output interface 1320 comprises an electrical connector, such as a universal serial bus. Output interface 1320 may further comprise an RFID transmitter. Output interface 1320 may further include a wireless link (e.g., WiFi, Bluetooth®, IR, RF, or other known wireless communication approaches, a direct wired connection (e.g. electrical wire or optical cable), or a direct connection via one or more direct lead contacts. Thus, output interface 1320 facilitates communication between disinfection device 1300 and a remote computer device, whereby information obtained by and stored on memory of disinfection device 1300 may be transferred to a remote computer device for long-term storage.

Input and output interfaces 1310 and 1320 may be located at any position on the housing of disinfection device 1300. In some embodiments, input and output interfaces are positioned such that a user may hold disinfection device 1300 in their hand and still have access to the interfaces. Input and output interfaces 1310 and 1320 may further comprises a separate device that is operably connected to disinfection device 1300 via a corded or wired connection, or a wireless connection. For example, input interface 1310 may comprises a wireless antenna that receives a signal from barcode scanner that is wirelessly connected to input interface 1310.

Figure 14:
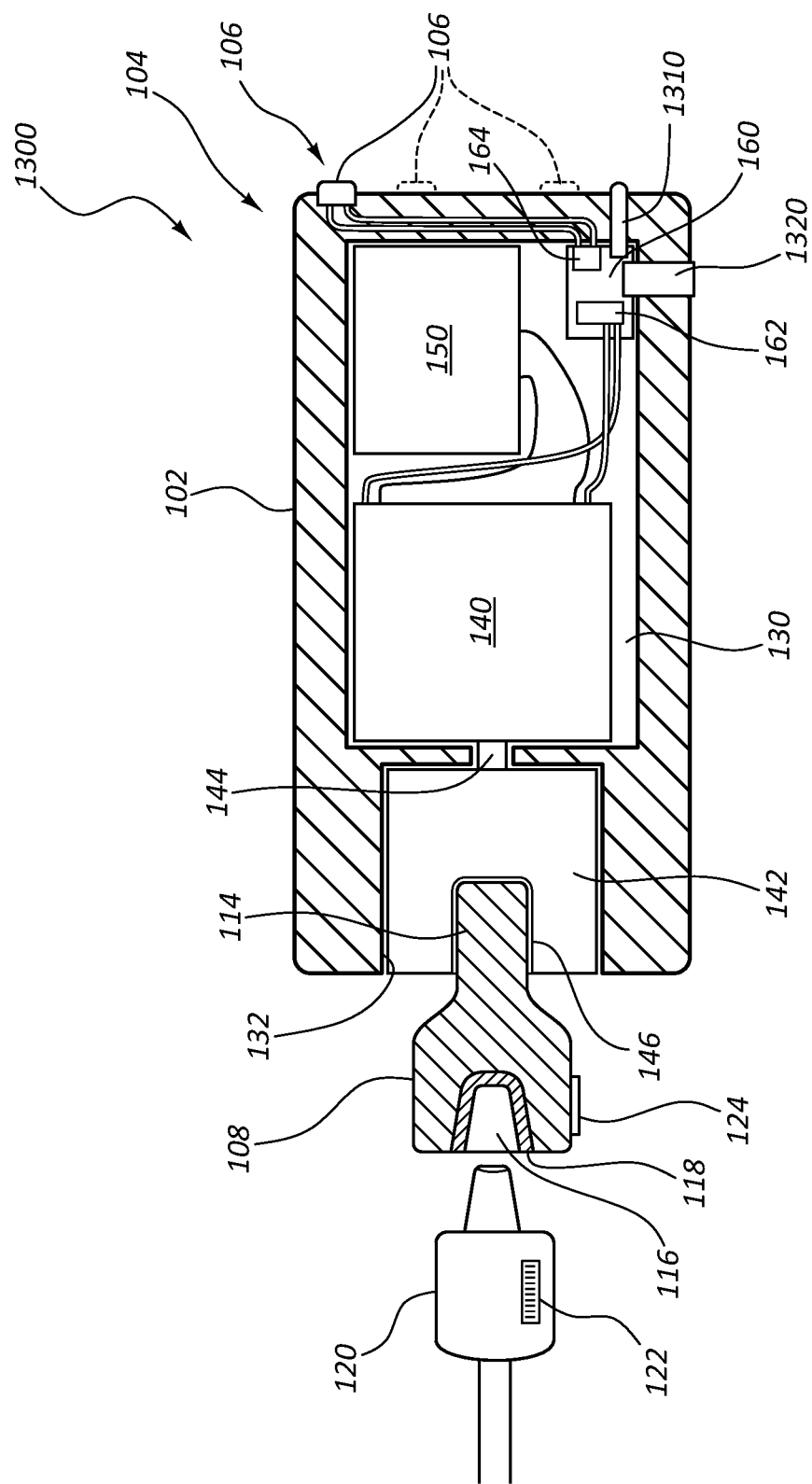
FIG. 14 is a cross-section top view of the handheld disinfection device of FIG. 8 in accordance with a representative embodiment of the present invention.

Referring now to FIG. 14, a cross-section view of disinfection device 1300 is shown. In some embodiments, input and output interfaces 1310 and 1320 are operably connected to the remaining components and circuitry of disinfection device 1300 via printed circuit board 160. Needleless connector 120 may further comprises one or more computer-readable codes 122 which may be scanned or otherwise read by input interface 1310 prior to commencing a disinfection event. In some embodiments, cleaning head 108 further comprises a computer-readable code 124 which contains information related to the identity and history of cleaning head 108 to prevent multiple uses of the disposable component.

In some instances, information retrieved from codes 122 and 124 are temporarily stored within memory of disinfection device 1300. The stored information may subsequently be transferred to a remote computer device via output interface 1320. In some embodiment, retrieved information is transferred to a remote computer device in real-time via output interface 1320. Input and output interfaces 1310 and 1320 may further be used to retrieve, record, and report information regarding the identity of a patient, wherein the patient information is contained in a computer-readable format. In some instances, the processes of recording and reporting the retrieved information is automatic, thereby eliminating user error.

In some embodiments, information regarding the identity of the patient and/or the needleless connector is entered manually into disinfection device 1300 or a remote computer device. For example, disinfection device 1300 may include a keyboard. Disinfection device 1300 may further include a microphone and transcription software, whereby a clinician may audibly enter information into disinfection device 1300. Disinfection device 1300 may further be operably connected to a separate input device, whereby the clinician is able to input information into disinfection device 1300 via the separate input device.

In some embodiments, the process of detecting a disinfection status, tracking a disinfection event, recording the disinfection event, and reporting the disinfection event may ensure compliance to proper cleaning procedures, thereby helping the clinical outcomes for patients and care providers. This information may further be stored in an electronic medical record (EMR) of the patient. As such, the disinfection event becomes part of the patient's medical history which may be accessible to other physicians and clinicians to assist in treatment of the patient. The information may further be accessed as part of an audit proceeding, such as a safety compliance audit. This information may further be accessed to assess areas, methods and techniques that may need revision to increase the quality and/or consistency of patient care.

Figure 15:
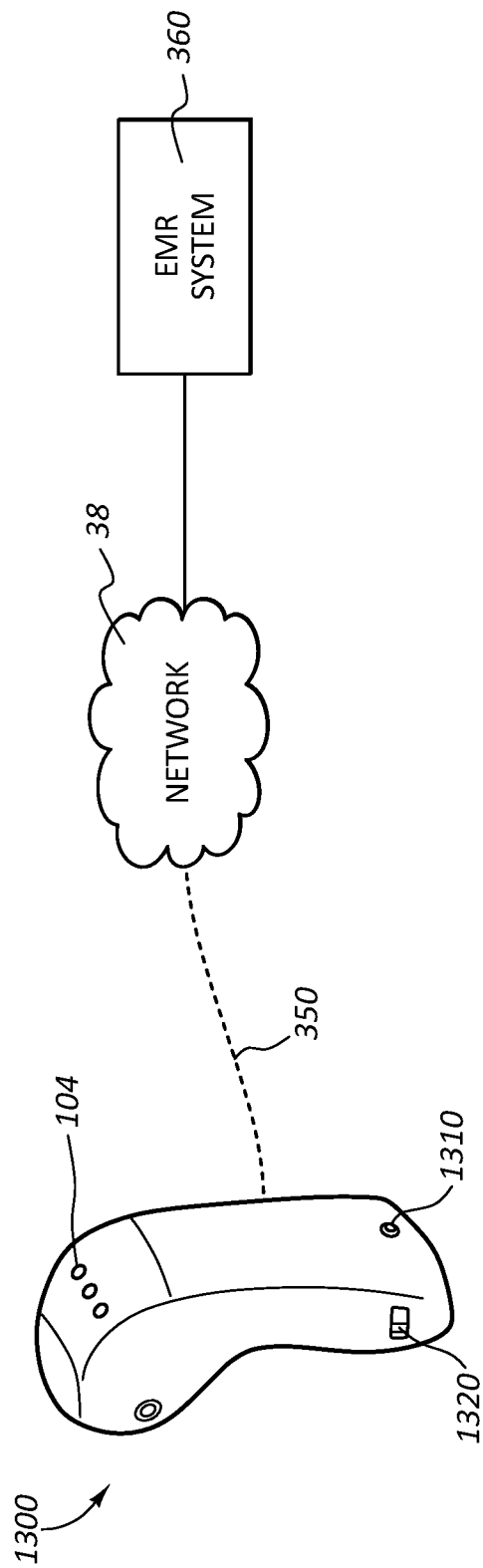
FIG. 15 is a diagrammatic view of a handheld disinfection device operably connected to an electronic medical record via a network in accordance with a representative embodiment of the present invention.

Referring now to FIG. 15, in some embodiments disinfection device 1300 is operably connected to a network 38 via a hardwired and/or wireless link 350. In some embodiments, link 350 comprises a portion of output interface 320. When information is acquired by disinfection device 1300, the information is transmitted to network 38 where the information is made accessible to various remote computer devices also operably connected to network 38. Further, in some embodiments acquired information is stored in a database, such as an EMR 360.

EMR 360 generally comprises a computerized medical record for a patient, as known in the art. In some embodiments, EMR 360 is configured to receive and store information relating to the disinfection event. For example, EMR 360 may receive information such as the date of the disinfection event, a final status of the disinfection event, the identity of the clinician who performed the disinfection event, the identity of the needleless connector, as well a time and/or duration of the disinfection event.

Network 38 may include a server on which a computer executable program is loaded having instructions for receiving, analyzing, and storing information received from disinfection device 1300. Network 38 may further include network security software or other precautionary software as may be required to comply with Health Information Patient Privacy Act requirements. In some embodiments, network 38 comprises a local area network. In other embodiments, network 38 is a global area network.

Figure 16:
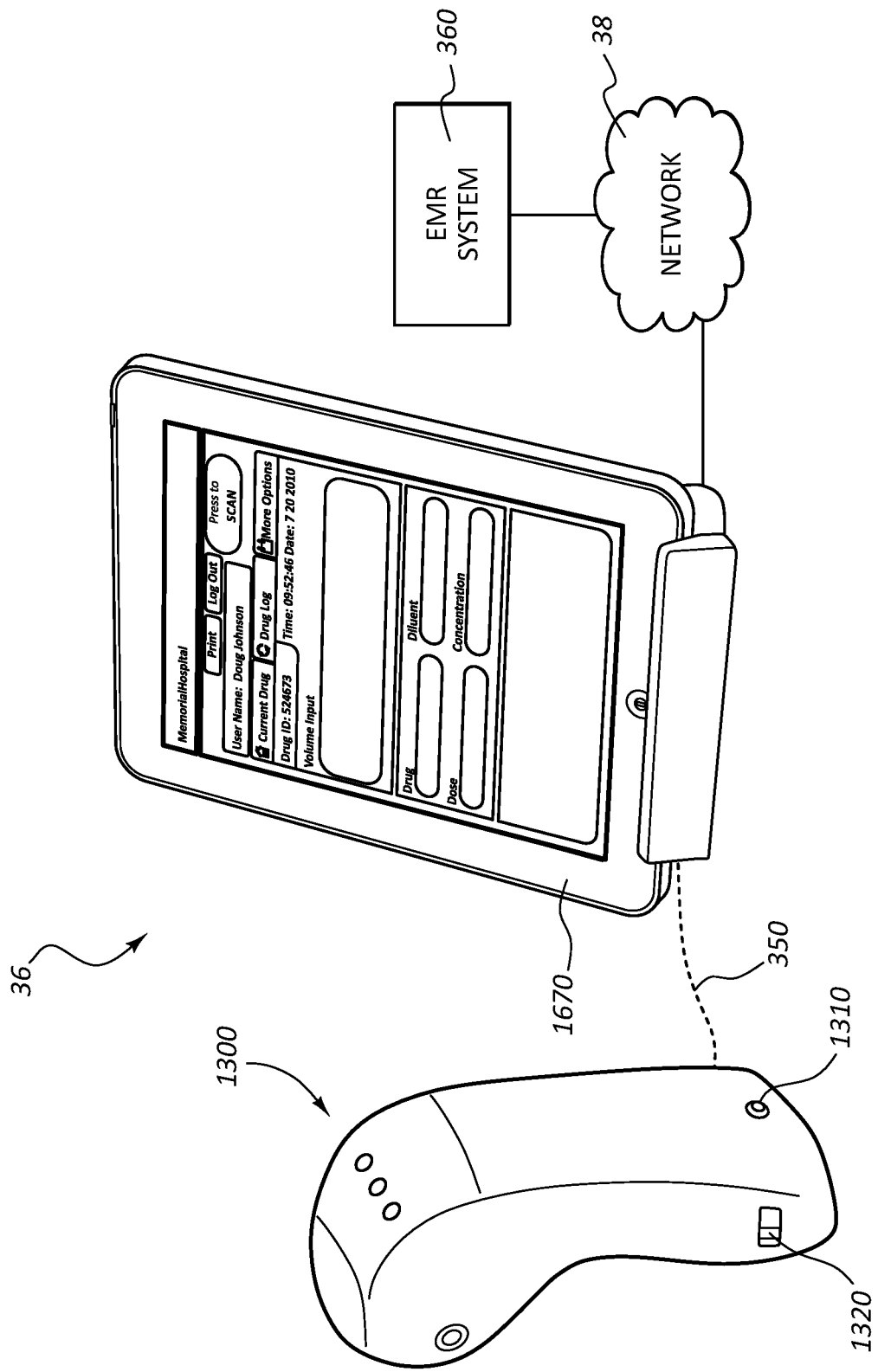
FIG. 16 is a diagrammatic view of a handheld disinfection device operably connected to an electronic medical record via a computer device and a network in accordance with a representative embodiment of the present invention.

In some configurations, disinfection device 1300 is operably connected to network 38 via a processor unit 1670 or other computer system, as shown in FIG. 16. Processor unit 1670 receives and processes retrieved information from output interface 1320 prior to storing the information in EMR 360. Processor unit 1670 may include any type or form of computing device which is compatible with the teachings of the present invention. In some embodiments, processor unit 1670 comprises a tablet computer. In other embodiments, processor unit 1670 comprises a desktop computer. Processor unit 1670 may further comprise a mainframe computer. Further still, in some embodiments processor unit 1670 comprises a mobile smart device, such as a smartphone, a tablet computer, or personal digital assistant device.

Figure 17:
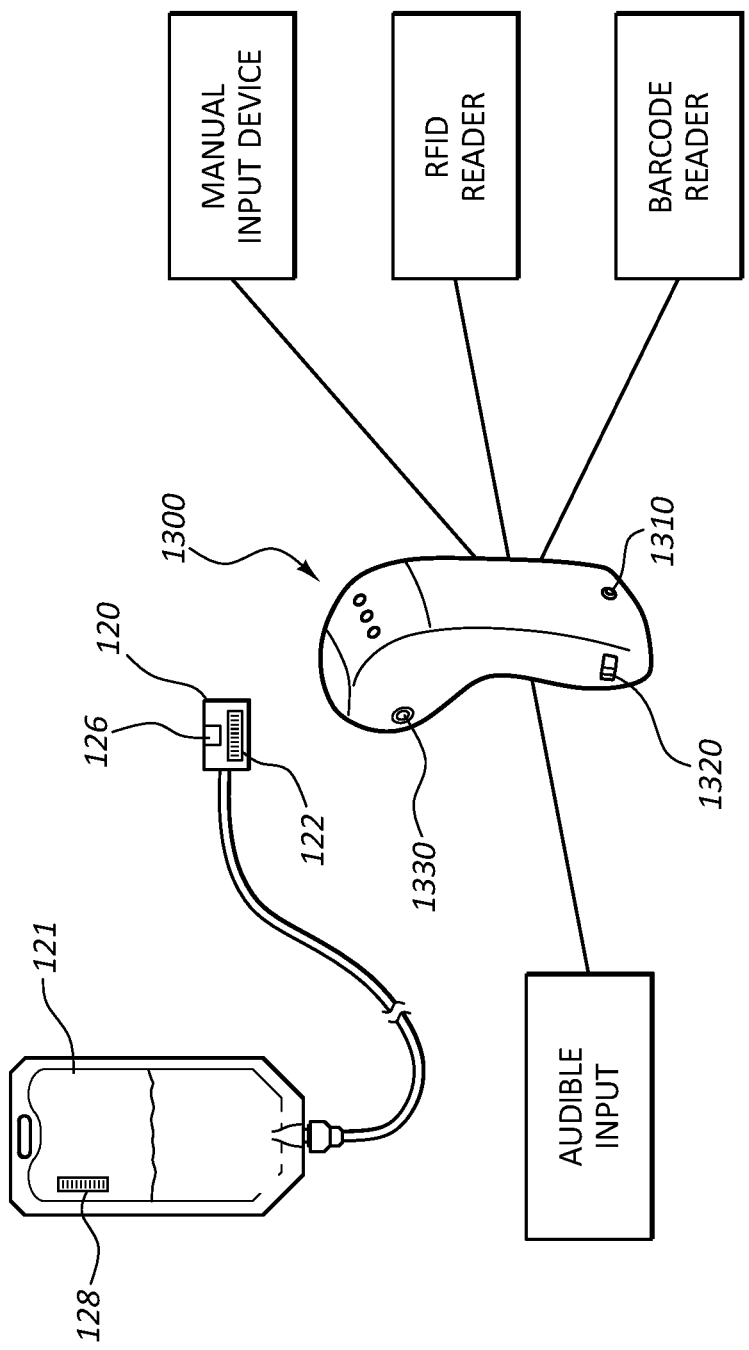
FIG. 17 is a diagrammatic view of a handheld disinfection device demonstrating various input and output features in accordance with a representative embodiment of the present invention.

Referring now to FIG. 17, disinfection device 1300 may include various systems and/or methods by which information relating to needleless connector 120 may be collected and reported. For example, in some embodiments disinfection device 1300 comprises input and output interfaces 1310 and 1320 which are capable of scanning a barcode 122 of needleless connector 120. Input and output interfaces 1310 and 1320 may further scan a barcode 128 of an IV fluid bag 121 coupled to needleless connector 120. In some instances, needleless connector 120 comprises an RFID chip 126. Accordingly, disinfection device 1300 may include an RFID reader. Disinfection device 1300 may further include an RFID transmitter whereby to report retrieved information to a computer device comprising an RFID receiver.

Input interface 1310 may further comprise a microphone 1330 whereby information is input by speaking the information into microphone 1330. The information may subsequently be reported or transferred to a remote computer device by any of the various output interfaces 1320 with which disinfection device 1300 is equipped. Accordingly, various embodiments of the present invention provide a disinfection device having one or more input interfaces 1310 and one or more output interfaces 1320, whereby information is retrieved by one or more of the input interfaces 1310 and subsequently transferred to a remote computer device via one or more of the output interfaces 1320.

Figure 18:
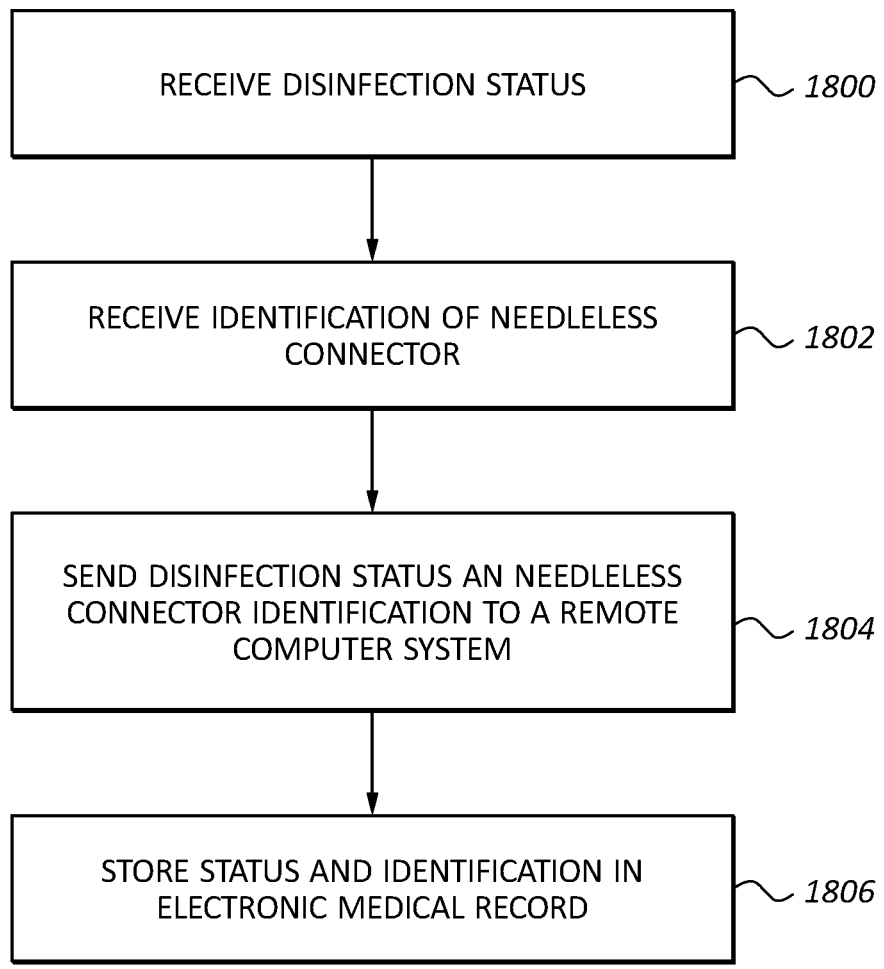
FIG. 18 is a flowchart demonstrating a method for monitoring, recording and tracking disinfection information in accordance with a representative embodiment of the present invention.

Referring now to FIG. 18, a method for monitoring, recording, and tracking disinfection information is shown. In some embodiments, a disinfection device of the present invention is configured to generate and store information regarding a disinfection status of a needleless connector that is being disinfected as part of a disinfection event (at step 1800). The disinfection device further comprises an input interface which is configured to receive an identification of the needleless connector (at step 1802). In some instances, the identification of the needleless connector is retrieved prior to commencing disinfection of the needleless connector. In other instances, the identification of the needleless connector is retrieved following a disinfection event.

The disinfection status and identity of the needleless connector are then sent to a remote computer system (at step 1804). The retrieved information is then stored in an electronic medical record of the patient for whom the needleless connector was disinfected (at step 1806).

Figure 19:
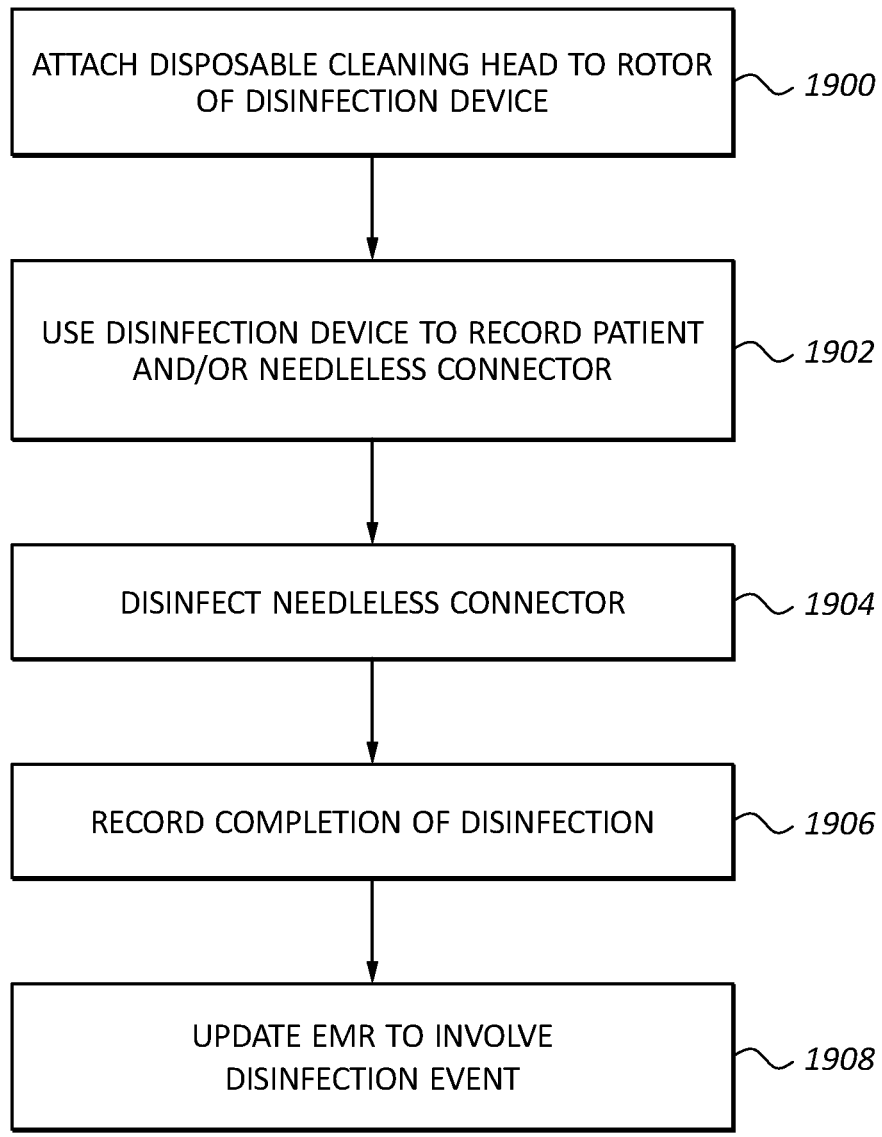
FIG. 19 is a flowchart demonstrating a method for monitoring and recording a disinfection event of a needleless connector in accordance with a representative embodiment of the present invention.

Referring now to FIG. 19, a method for monitoring and recording a disinfection event of a needleless connector is shown. In some embodiments, a method for monitoring a recording a disinfection event of a needleless connector comprises a first step of attaching a disposable cleaning head to a rotor of a disinfection device (at step 1900). In some embodiments, a clinician first uses an input interface of the disinfection device to retrieve information from the cleaning head which relates to the identity and history of the cleaning head. By tracking the disposable cleaning or disinfection head used in the disinfection process or event, a clinic may ensure that the disinfection or cleaning head has only been used once. Thus, cross-contamination between the cleaning head and subsequent needleless connectors is avoided.

The clinician then uses the disinfection device to retrieve and record information relating to the identity of the patient and/or the needleless connector (at step 1902). The clinician then disinfects the needleless connector using the disinfection device (at step 1904). In some embodiments, the disinfection device automatically records of the disinfection event, as well as other information relating to the disinfection event (at step 1906). For example, the disinfection device may automatically record error messages, date and timestamp information, and the identity of the clinician performing the disinfection event. The recorded information is then transferred to a remote computer device which processes the information and uploads the information to an electronic medical record (at step 1908).

The present invention may be embodied in other specific forms without departing from its structures, methods, or other essential characteristics as broadly described herein and claimed hereinafter. Thus, the described embodiments are to be considered in all respects only as illustrative, and not restrictive. The scope of the invention is, therefore, indicated by the appended claims, rather than by the foregoing description. All changes that come within the meaning and range of equivalency of the claims are to be embraced within their scope.

The invention claimed is:

1. A method for cleaning a needleless connector using disinfection device comprising:
   a housing;
   a motor slidably positioned within the housing between an active position and an inactive position, wherein in the active position a motor shaft of the motor rotates, and wherein in the inactive position the motor shaft is stationary;
   a hub coupled to the motor shaft and comprising a cleaning head having a distal opening forming an inner chamber configured to receive the needleless connector, the inner chamber further comprising a cleaning pad;
   a spring coupled to and interposed between the motor and the housing, wherein the spring biases the motor into the inactive position, and wherein compression of the spring slides the motor into the active position;
   a speed sensor configured to monitor and measure an axial rotation speed of the hub, wherein in response to measuring the axial rotation speed of the hub below a minimum axial rotation speed threshold, the speed sensor generates an error code;
   a status indicator operably connected to a status indicator controller configured to receive the error code, wherein in response to receiving the error code, the status indicator controller sends a first signal to the status indicator comprising at least one of a first color and a first lighted pattern; and
   a timer electrically coupled to the speed sensor and configured to measure a length of time for the hub to reach the minimum axial rotation speed threshold, wherein in response to measurement of the axial rotation speed above the minimum axial rotation threshold for a minimum time lapse threshold, the status indicator displays a second signal to the status indicator comprising at least one of a second color and a second lighted pattern, the method comprising steps for:
   selectively attaching the cleaning head to the hub via an attachment feature of the hub;
   inserting the needleless connector into the inner chamber of the hub; and
   pushing the needleless connector against the cleaning head with a force sufficient to compress the spring and thereby slide the motor within the housing from the inactive position to the active position, wherein the active position rotates the cleaning head to clean the needleless connector.

2. The method of claim 1, further comprising a step for preloading the cleaning pad with a cleaning agent prior to inserting the needleless connector into the inner chamber.

3. The method of claim 1, further comprising a step for removing the needleless connector from the inner chamber after the needleless connector is cleaned, wherein the step of removing the needleless connector from the inner chamber decompresses the spring, thereby sliding the motor within the housing from the active position to the inactive position.

4. The method of claim 3, further comprising a step for decoupling the cleaning head from the hub after the needleless connector is cleaned.

5. The method of claim 4, wherein the hub comprises a piston for decoupling the cleaning head from the hub.

6. The method of claim 4, further comprising a step for disposing the cleaning head after the step removing the needleless connector from the inner chamber.

7. The method of claim 1, further comprising a step for maintaining contact between the cleaning head and needleless connector while decoupling the cleaning head from the hub after the needleless connector is cleaned.

8. The method of claim 1, further comprising a step for disposing the cleaning head following a single use of the cleaning head.

9. The method of claim 1, further comprising a step for measuring an axial force on the motor.

10. The method of claim 1, further comprising a step for using a load cell of the disinfection device to measure an axial force on the motor.

11. The method of claim 1, further comprising a step for activating an axial load-sensitive switch of the disinfection device by sliding the motor from the inactive position to the active position, wherein the axial load-sensitive switch is interposed between the motor and the housing.

12. The method of claim 1, further comprising a step for detecting the presence of the needleless connector with a sensor of the disinfection device.

13. The method of claim 12, wherein the sensor is a light sensor.

14. The method of claim 1, further comprising a step for recording at least one of: i) a timestamp of a disinfection event, ii) an error code, and iii) an identity of a clinician performing a disinfection event.

15. The method of claim 1, further comprising a step for maintaining an axial rotation speed using an electronic speed control of the disinfection device.

16. The method of claim 1, further comprising a step for rotating the hub in an oscillatory rotational motion.

17. The method of claim 1, further comprising a step for magnetically attaching the cleaning head to the hub.

18. The method of claim 1, further comprising a step for changing a color of the hub in response to exposure to at least one of air and a liquid.

* * * * *